(12) United States Patent
Dubois et al.

(10) Patent No.: US 9,427,166 B2
(45) Date of Patent: Aug. 30, 2016

(54) PHYSIOLOGICAL MAPPING FOR ARRHYTHMIA

(71) Applicant: CARDIOINSIGHT TECHNOLOGIES, INC., Cleveland, OH (US)

(72) Inventors: Remi Dubois, Merignac (FR); Brian P. George, Medina, OH (US); Charulatha Ramanathan, Solon, OH (US); Qingguo Zeng, Solon, OH (US); Maria Strom, Moreland Hills, OH (US); Venkatesh Vasudevan, Beachwood, OH (US); Ryan Bokan, Boise, ID (US); Ping Jia, Solon, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 112 days.

(21) Appl. No.: 14/032,552

(22) Filed: Sep. 20, 2013

(65) Prior Publication Data

US 2014/0088395 A1     Mar. 27, 2014

Related U.S. Application Data

(60) Provisional application No. 61/704,227, filed on Sep. 21, 2012.

(51) Int. Cl.
*A61B 5/044*     (2006.01)
*A61B 5/04*     (2006.01)
(Continued)

(52) U.S. Cl.
CPC .............. *A61B 5/044* (2013.01); *A61B 5/046* (2013.01); *A61B 5/04012* (2013.01); *A61B 5/0464* (2013.01); *A61B 5/6823* (2013.01);
(Continued)

(58) Field of Classification Search
CPC ..................................................... A61B 5/044
See application file for complete search history.

(56) References Cited

U.S. PATENT DOCUMENTS

| 5,738,096 A | 4/1998 | Ben-Haim |
| 7,953,475 B2 | 5/2011 | Harlev et al. |

(Continued)

FOREIGN PATENT DOCUMENTS

| WO | 2007134190 A2 | 11/2007 |
| WO | 2011127211 A2 | 10/2011 |

(Continued)

OTHER PUBLICATIONS

Int'l Search Report and Written Opinion—7 pgs., Jan. 6, 2014, CardioInsight Technologies, Inc.

(Continued)

*Primary Examiner* — Carl H Layno
*Assistant Examiner* — Jennifer Ghand
(74) *Attorney, Agent, or Firm* — Tarolli, Sundheim, Covell & Tummino LLP

(57) ABSTRACT

A non-transitory computer-readable medium can have instructions executable by a processor. The instructions can include an electrogram reconstruction method to generate reconstructed electrogram signals for each of a multitude of points residing on or near a predetermined cardiac envelope based on geometry data and non-invasively measured body surface electrical signals. The instructions can include a phase calculator to compute phase signals for the multitude of points based on the reconstructed electrogram signals and a visualization engine to generate an output based on the computed phase signals.

20 Claims, 15 Drawing Sheets

(51) Int. Cl.
| | |
|---|---|
| *A61B 5/00* | (2006.01) |
| *A61B 18/14* | (2006.01) |
| *A61B 5/046* | (2006.01) |
| *A61B 5/0464* | (2006.01) |
| *A61B 5/0408* | (2006.01) |
| *A61B 17/00* | (2006.01) |
| *A61B 18/00* | (2006.01) |

(52) U.S. Cl.
CPC ........ *A61B18/1492* (2013.01); *A61B 5/04085* (2013.01); *A61B 5/4836* (2013.01); *A61B 5/7242* (2013.01); *A61B 5/7257* (2013.01); *A61B 2017/00044* (2013.01); *A61B 2017/00053* (2013.01); *A61B 2018/00839* (2013.01); *A61B 2018/00869* (2013.01)

(56) References Cited

U.S. PATENT DOCUMENTS

| | | |
|---|---|---|
| 2002/0038093 A1 | 3/2002 | Potse et al. |
| 2004/0059237 A1 | 3/2004 | Narayan et al. |
| 2005/0059880 A1 | 3/2005 | Mathias et al. |
| 2006/0183999 A1 | 8/2006 | Lorenz et al. |
| 2007/0021679 A1 | 1/2007 | Narayan et al. |
| 2009/0299424 A1 | 12/2009 | Narayan |
| 2010/0074485 A1 | 3/2010 | Movassaghi et al. |
| 2010/0094274 A1 | 4/2010 | Narayan et al. |
| 2011/0040178 A1 | 2/2011 | Brunner et al. |

FOREIGN PATENT DOCUMENTS

| | | |
|---|---|---|
| WO | 2012061612 A2 | 5/2012 |
| WO | 2011127209 A1 | 10/2013 |

OTHER PUBLICATIONS

Ravi Mandapati, MD, et. al., "Stable Microreentrant Sources as a Mechanism of Atrial Fibrillation in the Isolated Sheep Heart", Publication, Departments of Pharmacology and Pediatrics, Jul. 23, 1999, pp. 194-199.

Sharon Zlochiver, PhD, et al., "Rotor Meandering Contributes to Irregularity in Electrograms During Atrial Fibrillation", NIH Public Access, Author Manuscript, Jun. 2008, pp. 1-14.

José Jalife, et al., "Motor rotors and Fibrillatory Conduction: A Mechanism of Atrial Fibrillation", Elsevier Science B.V., May 2002, pp. 204-216.

Richard A. Gray, et al., "Spatial and Temporal Organization During Cardiac Fibrillation", Department of Pharmacology, SUNY Health Science Center, Nature, vol. 392, Mar. 1998, pp. 75-78.

Jack M. Rogers, "Combined Phase Singularity and Wavefront Analysis for Optical Maps of Ventricular Fibrillation", IEEE, Jan. 2004, pp. 56-65.

Sanjiv M. Narayan, M.Sc., M.D., et al., "Clinical Mapping Approach to Diagnose Electrical Rotor and Focus Impulse Sources for Human Atrial Fibrillation", Manuscript, Veterans' Affairs and University of California Medical Centers and Institute for Theoretical Biological Physics, May 2012, pp. 1-8.

Jay Chen, et al., "Dynamics of Wavelets and their Role in Atrial Fibrillation in the Isolated Sheep Heart", Elsevier Science B.V., Jun. 28, 2000, pp. 220-232.

C.S. Daw, et al., "A Review of Symbollic Analysis of Experimental Data", www-chaos.engr.utk.edu/pap/crg-rsi2002.pdf, Jul. 22, 2002, pp. 1-18.

Karthikeyan Umapathy, et al., "Phase Mapping of Cardiac Fibrillation", Circulation Arrhythmia and Electrophysiology-American Heart Association, Mar. 2010, Supplemental: 2010, 17 pp.

Mark-Anthony P. Bray, "Visualization and Analysis of Electrodynamic Behavior During Cardiac Arrhythmias", Dissertation, Graduate School of Vanderbilt University, May 2003, 128 pp.

James R Keener, "A Mathematical Model for the Vulnerable Phase in Myocardium", Mathematical and Computer Modelling, Jan. 1, 1989, pp. 1178-1178, XP055259101, DOI: 10.1016/0895-7177(89)90245-8 Retrieved from the Internet: URL:http://ac.els-cdn.com/0025556488900557/1-s2.0-0025556488900557-main.pdf?_tid=0fab7ff6-ec1e-11e5-95f4-00000aacb361&acdnat=1458205136_f7023bb46cca4ab3443e5b615fcf38a1 [retrieved on Mar. 17, 2016] *the whole document*.

Robert Modre*, et al, "Noninvasive Myocardial Activation Time Imagining: A Novel Inverse Algorithm Applied to clinical ECG Mapping Data", IEEE Transactions on Biomedical Engineering, IEEE Service Center, PISCATAWAY, NJ, USA, vol. 49, No. 10, Oct. 1, 2002, XP011070403, ISSN: 0018-9294 *the whole document*.

Supplementary European Search Report, Applicant: Cardiolnsight Technologies, Inc., Application No. EP13838803, Filed Sep. 20, 2015, Date of Completion of the Search: Mar. 17, 2016, pp. 1-8.

PHYSIOLOGICAL MAPPING FOR ARRHYTHMIA

CROSS-REFERENCE TO RELATED APPLICATION

This application claims the benefit of priority from U.S. Provisional Patent Application No. 61/704,227, filed Sep. 21, 2012, and entitled PHYSIOLOGICAL MAPPING FOR ARRHYTHMIA, which is incorporated herein by reference in its entirety.

TECHNICAL FIELD

This disclosure relates to physiological mapping for arrhythmia, such as fibrillation or tachycardia.

BACKGROUND

Electrocardiographic mapping (ECM) is a technology that is used to determine and display heart electrical information from sensed electrical signals. Mapping of cardiac electrical activity becomes further complicated in the presence of certain types of arrhythmia such as fibrillation, including atrial and ventricular fibrillation. The cardiac signal contains several consecutive depolarizations of the tissue. Most methods in practice today that describe analysis of cardiac depolarization or activation rely on a priori knowledge of periodicity or cycle length of the signal (e.g., for 3D activation mapping). In cardiac activations where there is no specific periodicity or cycle length, analysis techniques such as phase mapping have been developed. However, existing phase mapping approaches are invasive, such as including a basket catheter(s) inserted into the heart or injecting dye into the heart muscle and performing optical imaging. Optical imaging dyes are toxic in humans, and the resolution provided by basket catheters is not sufficient to generate an accurate phase map of human atria.

SUMMARY

This disclosure relates to physiological mapping for arrhythmia, such as fibrillation or tachycardia.

As one example, a system can include memory to store machine readable instructions and data, and a processor to access the memory and execute the instructions for performing a method. The method can include converting processed electrical data, corresponding to non-invasive electrical data obtained from a patient for at least one time interval, to corresponding reconstructed electrical signals on a predetermined cardiac envelope. The reconstructed electrical signals can be spatially and temporally consistent. The method can also include computing phase data based on the reconstructed electrical signals.

As another example, a non-transitory computer-readable medium can have instructions executable by a processor. The instructions can include an electrogram reconstruction method to generate reconstructed electrogram signals for each of a multitude of points residing on or near a predetermined cardiac envelope based on geometry data and non-invasively measured body surface electrical signals. The instructions can include a phase calculator to compute phase signals for the multitude of points based on the reconstructed electrogram signals and a visualization engine to generate an output based on the computed phase signals.

DETAILED DESCRIPTION

This disclosure relates to non-invasive electrophysiological mapping for arrhythmia, such as fibrillation. The mapping technology can be used as part of a diagnostic and/or treatment workflow to facilitate identifying and locating of fibrillation mechanisms based on non-invasive body surface measurements of body surface electrical activity. The non-invasive body surface measurements can be utilized to reconstruct high resolution electrical signals on a cardiac envelope, such as the heart surface. The approach disclosed herein can employ signal processing techniques, including processing before, during and/or after computing an inverse solution relative to the electrical data. Such signal processing enables high resolution outputs from which treatment targets can be identified without the use of invasive measurement catheters or injecting dye as in optical mapping.

The approach disclosed herein can also be utilized in real time (e.g., to provide guidance during an electrophysiology study or during delivery of a therapy) or it can be implemented in relation to stored electrical data previously acquired for a given patient. The signal processing can extract physiologically relevant information from the non-invasive electrical data and compute the phase over one or more time intervals. The computed phase can be utilized to identify and characterize fibrillation mechanisms including but not limited to focal points, triggered activity, micro and macro-reentrant circuits and localized rotors in a patient's heart. The resulting phase data can also be utilized to generate a graphical visualization to present spatially and temporally consistent information from one or more maps. The mapping outputs can be further graphically represented as 3D anatomical maps including dynamic animated movies depicting rotors and associated movement as well as other characterizations of temporally and spatially consistent arrhythmia perpetuators as clinical targets.

Figure 1:
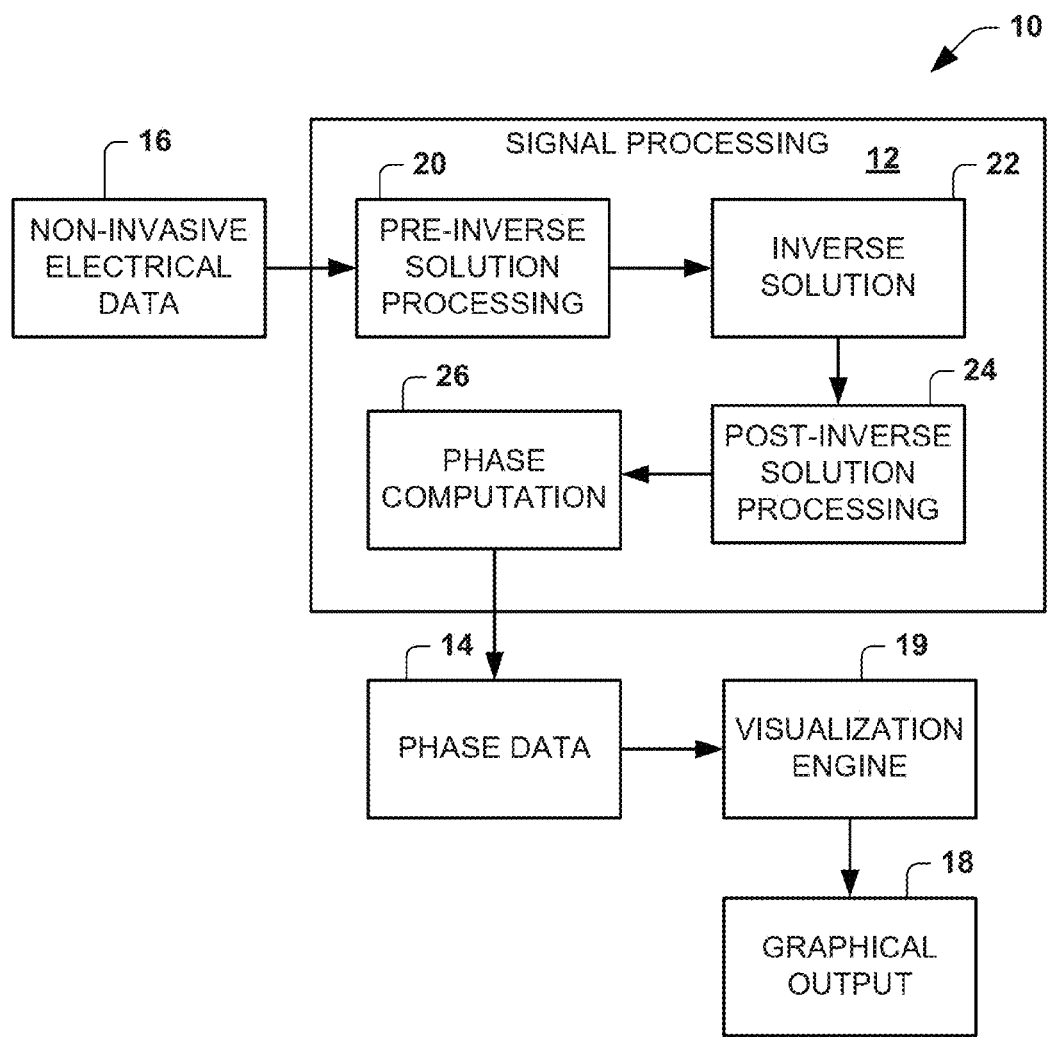
FIG. 1 depicts an example of a system for performing phase mapping for arrhythmias.

FIG. 1 depicts an example of an electrocardiographic mapping system 10. The system 10 includes signal processing methods 12, which can be stored in a non-transitory machine readable medium as instructions that are executable by a processor. The signal processing methods 12 are programmed to compute phase data 14 based on non-invasive electrical data 16. The non-invasive electrical data 16 can correspond to stored electrical data that has been acquired non-invasively in advance and stored in memory for subsequent processing. Alternatively, the non-invasive electrical data 16 can correspond to a real time data flow that can be acquired by non-invasive (e.g., body surface) electrodes during a procedure such as during an electrophysiological study as well as during a treatment procedure that can include cardiac ablation. The generated phase data 14 can be stored in memory and correspond to the phase of electrical activity for each of a plurality of identified locations across a three-dimensional cardiac envelope. Such cardiac envelope can correspond to an epicardial surface, and endocardial surface or an arbitrary 3-D envelope having a known relative position in three dimensions with respect to a patient's heart.

The system 10 can include a visualization engine 19 that is programmed to generate a corresponding visualization demonstrated as a graphical output 18. The output 18, for example, can include a phase map that is generated based on phase data 14 computed for the points distributed across the cardiac envelope. Additionally or alternatively, the phase data 14 can correspond to phase singularities (e.g., rotor cores) or other phase characteristics that are calculated based on the signals represented by the non-invasive electrical data 16. For instance, the graphical output 18 can include a map depicting an integral of phase gradient demonstrating spatial and temporal consistency of a rotor core (e.g., an integral phase gradient map). Unlike existing invasive technologies, the integral phase map can be spatially and temporally consistent for multiple chambers of the heart (e.g., as to present bi-atrial or bi-ventricular phase characteristics simultaneously).

As another example, the visualization engine 19 can generate a phase map in a movie or cinematographic format to demonstrate rotor movement and interactions dynamically over a period of one or more time intervals. In still other examples, the visualization engine 19 can generate graphical outputs and maps based on other data such as may include potential maps, activation maps, dominant frequency maps or the like. Such additional maps relating to the electrical potential activity can be combined with the phase data into a single display. Alternatively or additionally, the visualization engine 19 can concurrently generate multiple displays in which the phase map or related phase characteristics are displayed in a window or display that is adjacent to the potential-based electrocardiographic mapping (e.g., activation maps, dominant frequency maps or the like).

In the example of FIG. 1, the signal processing 12 can include a plurality of steps (e.g., program modules) that can be executed for processing the non-invasive electrical data 16 to generate the phase data 14. For example, pre-inverse solution processing (also referred to herein as preprocessing) 20 can be applied to the non-invasively acquired electrical data 16 such as to extract relevant parts (or remove irrelevant parts) of each signal that is contained in the non-invasive electrical data 16 for subsequent processing. The preprocessing 20 thus can provide preprocessed electrical data that is utilized to drive the inverse solution 22.

The inverse solution method 22 can compute reconstructed electrograms on a cardiac envelope based on the preprocessed electrical data and geometry data (not shown) that are supplied to the inverse solution. The geometry data can correspond to actual geometry data acquired for a given patient, a general anatomical model or a combination thereof. The pre-inverse solution processing 20 can provide the preprocessed electrical data to increase specificity for each particular type of arrhythmia (e.g., atrial fibrillation (AF), atrial tachycardia (AT), ventricular fibrillation (VF), ventricular (VT)) for which the phase data 14 is being computed while decreasing the overall sensitivity of the input data that is supplied to the inverse solution 22. In addition to removing signal features via the pre-inverse solution processing 20, such preprocessing can also remove noise (e.g., noise corresponding to undesired oscillations) from each signal channel via filtering such as notch filtering, low pass filtering and removing bad channels.

As an example, the pre-inverse solution processing 20 can be programmed to remove signal contributions due to ventricular function (e.g., depolarization of one or both ventricles, repolarization of the ventricles or both) when computing phase data for AF. For example, the feature extraction for removing signal features due to ventricular electrical activity can be implemented by QRS-wave cancellation and/or cancellation of T-waves (e.g., the QT interval or a selected portion thereof) in signals before computing the inverse solution 22 to reconstruct electro grams on the cardiac envelope. Such cancellation can remove the entire portion of the wave or any a portion sufficient to increase the specificity of selected other signal components of interest. It is to be understood that in addition to signal preprocessing 20 other methods can be utilized to mitigate the effects of ventricular signals while computing values for AF phase diagnostics. Such methods can include use of chemicals (e.g., drugs), electrical stimulation and combinations thereof. The type of preprocessing 20 further can be programmed to remove unwanted signal content from the non-invasively acquired electrical signals depending on which type of arrhythmia is being analyzed.

As disclosed herein, the inverse solution 22 is programmed to provide reconstructed electrograms based upon preprocessed data. Examples of inverse algorithms that can be utilized in the system 10 are disclosed in U.S. Pat. Nos. 7,983,743 and 6,772,004, which are incorporated herein by reference. The inverse solution 22 can reconstruct the electrical activity onto a multitude of locations on a cardiac envelope (e.g., greater than 1000 locations, such as about 2000 locations or more). As a result, the phase data 14 that is provided by the processing can have a corresponding high resolution that is significantly greater than can be realized by invasive methods (e.g., via contact electrodes on a basket catheter). Additionally, the phase data 14 can be much safer than those generated using optical mapping techniques that use poisonous chemical dyes. By implementing the preprocessing 20 to remove unwanted information from the input signals represented by the non-invasive electrical data 16, the inverse solution 22 can be applied to the remaining signal information to provide corresponding electrical signals reconstructed on the cardiac envelope specially adapted with increased specificity for a selected type of phase analysis.

Additional post-inverse solution processing 24 can be applied to the reconstructed electrical data. The post-inverse solution processing 24 can include one or more filtering methods such as can include baseline removal, bandpass filtering and low pass filtering (see, e.g., FIG. 4).

Phase computation 26 can be programmed to calculate the phase data 14 from the filtered reconstructed electrogram data. For example, the phase computation 26 can implement signal decomposition to calculate the phase signals for each of the plurality of points across the surface of the cardiac envelope based on the filtered electrogram data. The phase computations can be implemented according to various solutions, such as disclosed herein (e.g., see phase computations described with respect to FIG. 8).

As disclosed herein, the visualization engine 19 further can compute the phase map and other visualizations based upon the phase signals computed for each location across the cardiac envelope. The phase map can be considered a true panoramic phase map for the cardiac envelope (e.g., the entire epicardial surface) since the input non-invasive electrical data 16 from which the phase signals are calculated can present spatially and temporally consistent phase information across the entire surface of the patient's heart or other user-selected region of interest. Since the panoramic visualization can provide spatially and temporally consistent information for the entire heart, spatial movement of rotors and interactions across the heart, including across multiple chambers, can be identified in contrast to existing invasive phase mapping techniques. For example, the visualization engine 19 can generate the graphical output 18 from the phase data 14 to include bi-ventricular and/or bi-atrial maps to characterize fibrillation mechanisms across multiple heart chambers.

The graphical output 18 can correspond to phase information at a given instant in time or it can be animated to show changes in phases across the cardiac envelope as a function of time. For instance, the time period further can include a continuous time period or it can include multiple temporally spaced apart time intervals (e.g., separate intervals spaced apart by minutes, hours or even days) according to how and when the non-invasive electrical data is acquired. Despite such delays between measurements, the phase data 14 generated can still be spatially consistent for each measurements set. Such an approach would not be feasible via existing invasive techniques without dramatically increasing patient risk. The changes can correspond to the cardiac electrical activity from one or more time intervals. A given time interval can include one or more phase cycles for each of the locations for which the phase data is computed.

Figure 2:
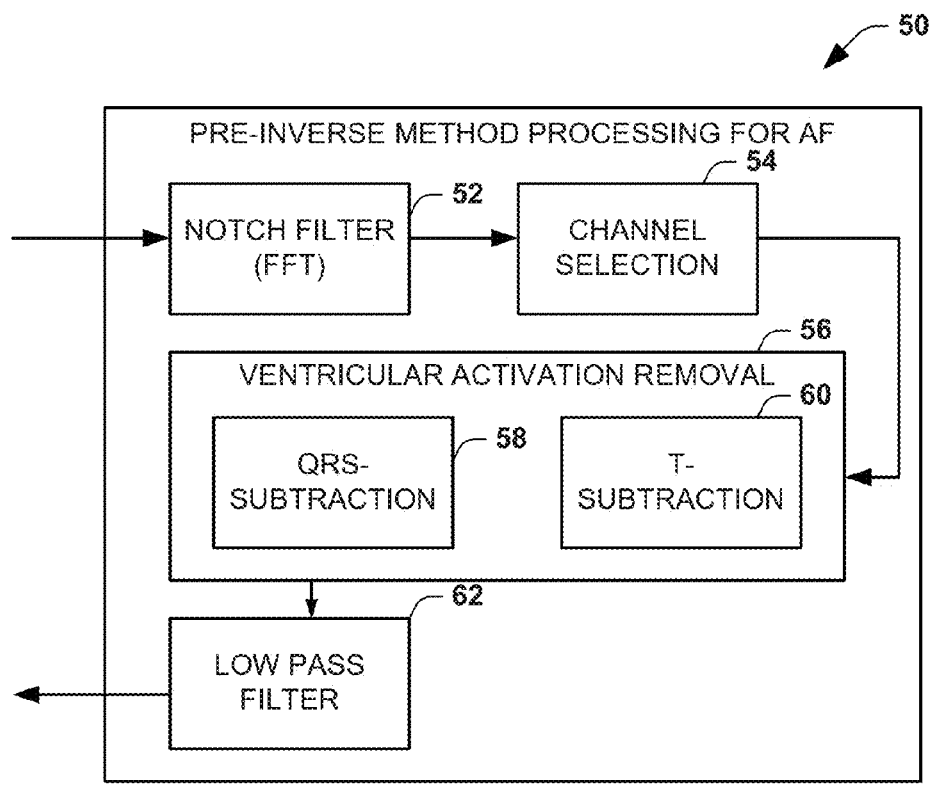
FIG. 2 depicts an example of pre-inverse solution processing that can be implemented for atrial fibrillation.

FIG. 2 depicts an example of pre-inverse solution processing (e.g., corresponding to preprocessing 20 of FIG. 1) 50 that can be configured to facilitate analysis of atrial fibrillation (AF) 50. The method 50 receives non-invasive electrical data, such as from a vest or other electrical array of sensors that can be distributed across a surface of a patient's torso. The method 50 includes a notch filter 52 that can be configured to remove line filter frequency and harmonics and other frequency ranges that can be specified by a user in response to a user input. Thus the notch filter 52 can be programmable. In some examples, the notch filter 52 can be implemented using a fast Fourier transform (FFT) method. The filtered data can be provided to the channel selection block 54 that can be utilized to select which input channels are to be utilized in subsequent processing.

The channel selection 54, for example, can include bad channel detection and removal. Bad channel detection can identify any channel that is determined to be detrimental to the calculation of the inverse solution (e.g., inverse solution 22 of FIG. 1). For example, bad channels can be disconnected channels, missing channels as well as channels with distorted data. The channel selection 54 can be implemented, for instance, by visual inspection of signals and/or by an automatic bad channel detection algorithm. Additionally or alternatively, channel selection 54 can be implemented to select a set of input channels corresponding to one or more regions of a patient's torso where signals being sensed have been predetermined to contribute positively to the type of analysis (e.g., AF or AT) and evaluation that is being performed on the heart or a selected region of interest.

The filtered data for the select channels can be provided to a ventricular activation removal block 56 to remove signal features corresponding to ventricular activation. As an example, the ventricular activation removal 56 can include a QRS-wave subtraction method 58. For example, the QRS subtraction can be implemented by a principal component analysis for virtual leads, locating template regions for a QRS-wave, averaging template regions, creating a corresponding region of interest template, dynamically adjusting the template and subtracting the adjusted template at the detected template regions from the filtered input signals.

Additionally or alternatively, the ventricular activation removal 56 can include T-wave subtraction 60 that is performed on the filtered signals provided by the selected channels. The T subtraction can be similar to the QRS-wave subtraction 58 but can use a different template that is configured corresponding to that of the T-wave. Alternatively, a single template corresponding to both the QRS-wave and the T-wave can be used to remove both QRS and T-waves from the filtered input signals provided for the selected channels.

The ventricular activation removal 56 thus can provide a processed signal that includes the portion of the signal identified relevant for the corresponding atrial analysis. By subtracting such features from the signals, some level of sensitivity may be sacrificed for increased specificity of phase analysis that is being implemented. The ventricular activation removal 56 can provide the corresponding signal to a low pass filter 62 that can be configured to pass bands below a predetermined cutoff frequency such as about 40 Hertz. As one example, the low pass filter 62 can be implemented as a Savitzy Golay filter. Other types of filters can also be utilized.

Figure 3:
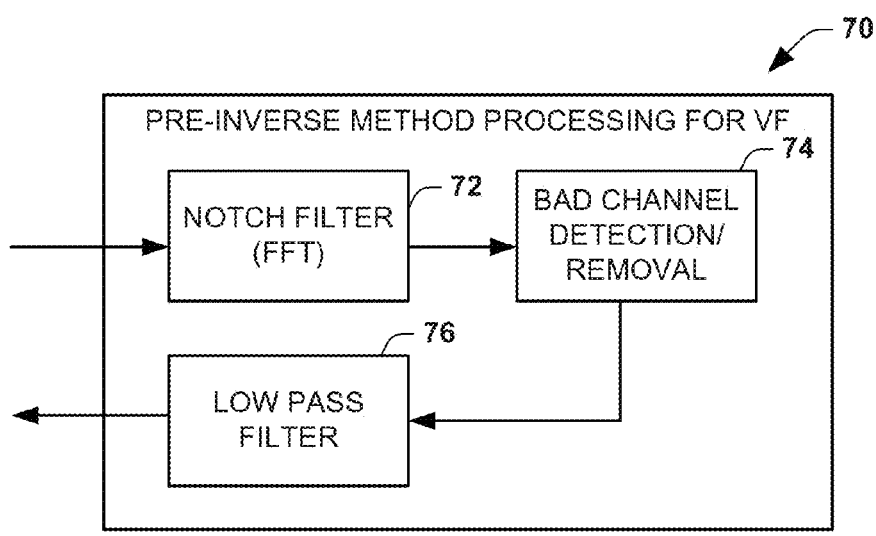
FIG. 3 depicts an example of a pre-inverse solution processing that can be implemented for ventricular fibrillation.

FIG. 3 depicts an example of a pre-inverse solution processing 70 that can be implemented to facilitate analysis of ventricular arrhythmia (e.g., VF or VT), such as can correspond to the pre-inverse solution processing 20 of FIG. 1. With more than one type of different pre-inverse solution processing, the approach disclosed herein can selectively control which type of preprocessing is performed according to the diagnostics and evaluations being performed, which can be selected in response to a user input.

In the example of FIG. 3, the pre-inverse solution processing 70 includes a notch filter 72 such as can be implemented using an FFT method. The notch filter 72 provides corresponding filtered signal to channel selection block 74 that can be configured to select which channels are utilized or removed from subsequent processing. For example, the channel selection block 74 can also be configured to retain channels in the input data determined to contribute more to ventricular activity than to atrial activity. Additional signal subtraction or filtering could be utilized to remove atrial features from the non-invasive input data (e.g., input data 16 of FIG. 1). The channel selection 74 can provide filtered signals for the selected channels to a low pass filter 76 to provide a corresponding filtered output that includes signal components of interest for performing phase diagnostics for evaluating ventricular arrhythmia.

Figure 4:
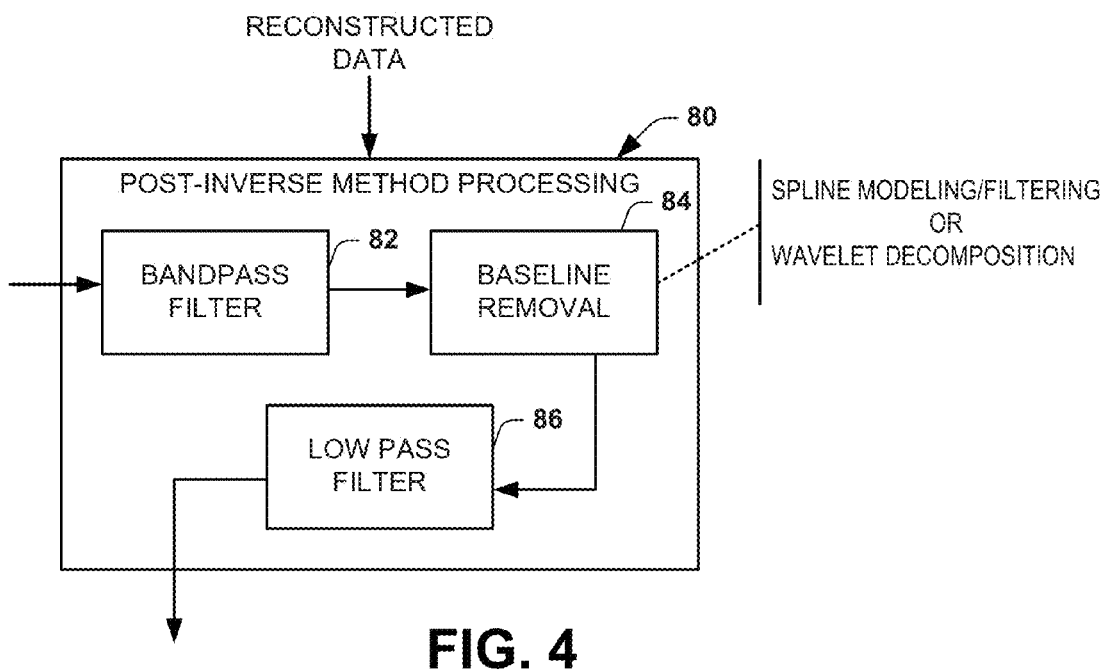
FIG. 4 depicts an example of post-inverse solution processing.

FIG. 4 depicts an example of a post-inverse method processing 80, which can correspond to the post-inverse solution processing 24 of FIG. 1. The post-inverse method processing 80 can be applied to reconstructed electrogram data corresponding to electrical activity on a cardiac envelope (e.g., the epicardial surface of a patient's heart). The post-inverse method processing 80 can include a bandpass filter 82 that is programmed to pass one or more bands at specified frequencies. As one example, the bandpass filter 82 can be implemented as a FIR filter.

The bandpass filtered signal can be provided to a baseline removal function 84 that is configured to remove baseline wander from the filtered signal. For example, the baseline wander cancellation can be performed by subtraction of a mean value of the signal, such as for atrial signals. In another example, the baseline removal 84 can be implemented by a method programmed to interpolate the baseline with a polynomial function. As an example, to remove the baseline wander, an interpolation of the baseline can be computed from anchor points selected on each signal.

Figure 5:
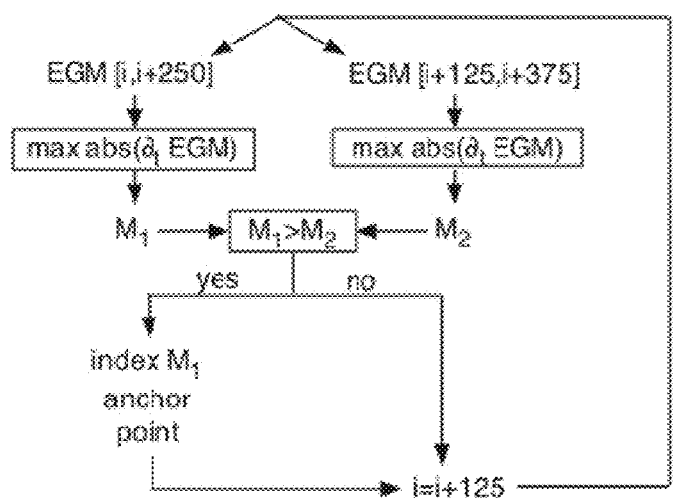
FIG. 5 depicts an example of a methodology that can be utilized as part of a baseline removal process.

An example of a methodology that can be utilized to remove the baseline is demonstrated in FIG. 5. Following the methodology in FIG. 5, a spline interpolation can be performed to link the anchor points from the given signal and then the resulting baseline can be subtracted from the given signal. Each resulting base-line corrected signal can then be passed through a low pass filter 86 to provide a corresponding process signal for subsequent calculations, including phase computations (e.g., via phase computation 26 of FIG. 1).

As yet another example, the baseline removal 84 can be implemented via wavelet decomposition such as by employing the plurality of levels of decomposition. For instance, the filtered signal can be decomposed onto a base of orthogonal wavelets, such as by employing a high order coiflet or other wavelet (e.g., Mexican hat or Morlet wavelets).

By way of further example, let x be the temporal signal. The wavelet decomposition leads to scale functions $s_i$ such that:

$$x(t) = \sum_{i=1 \ldots N_W} s_i(t) + r(t) \qquad \text{Eq. 1}$$

where r is the residuum function.
The filtering 84 can be performed by removing the $s_i$ functions from the sum that models non relevant information for the diagnostic. One method to such end can be to compute the Fourier Transform of each $s_i$ function, and to remove those functions that have a dominant frequency (e.g., frequency of the highest peak) outside the range of physiological frequencies (e.g., usually about 4 to 10 Hz). Thus, both low frequency components from the baseline and high frequency components from the noise can be removed. Additionally, such wavelet filtering operates to decompose a highly undulating waveform and remove components that contribute the unwanted oscillations, such that the signal can be reconstructed using only the components that reliably correspond to AF cycle lengths—such that the data includes signal components that correspond to true atrial depolarizations.

Figure 6:
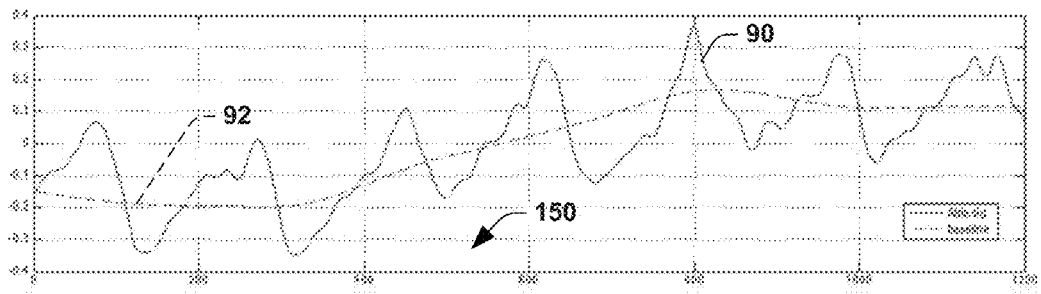
FIG. 6 depicts an example of an atrial signal and a corresponding baseline signal.

FIG. 6 demonstrates an example of an atrial signal 90 along with a corresponding baseline signal 92 that has been computed, such as according to one of the approaches disclosed herein. For each signal, the computed baseline signal 92 can be subtracted from the respective signal 90 to provide a corresponding signal that is substantially free from baseline drifting.

Figure 7:
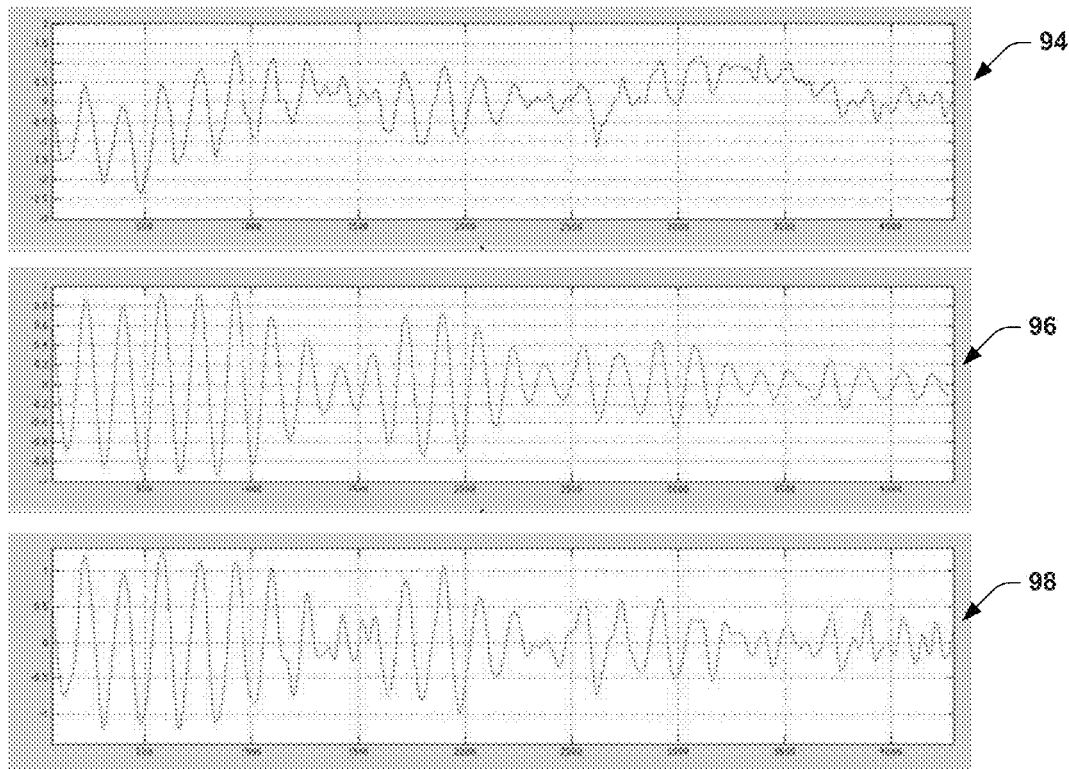
FIG. 7 depicts plots of ventricular signals before and after filtering.

FIG. 7 demonstrates an example of signal plots 94, 96 and 98 that can be provided via the post-inverse solution processing 80 of FIG. 4. In FIG. 7, a raw ventricular fibrillation signal 94 is shown. FIG. 7 also shows a signal 96 following frequency filtering to remove oscillations due to noise. FIG. 6 also demonstrates a signal 98 following wavelet filtering to mitigate baseline wander such as disclosed herein.

Figure 8:
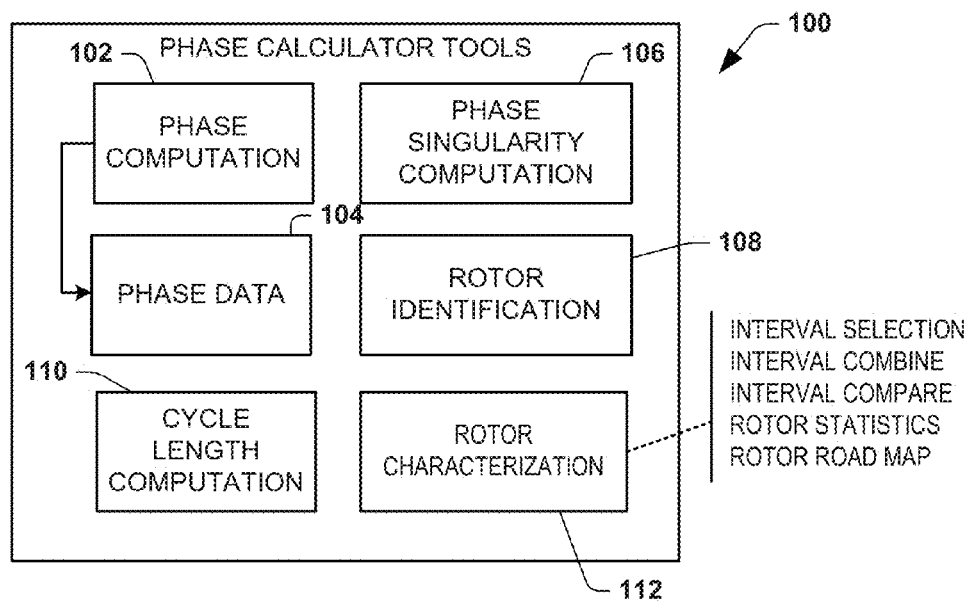
FIG. 8 depicts an example of phase calculator tools that can be implemented for generating phase data for use in generating a visualization.

FIG. 8 depicts an example of phase calculator tools 100 that can be programmed to perform methods for computing phase and phase characteristics from the processed reconstructed electrogram data (e.g., corresponding to signals provided by the method 24 of FIG. 1 or the method 80 of FIG. 4). The phase calculator tools 100 can be activated in response to a user input, such as via a graphical user interface (GUI) that provides access to the respective methods demonstrated with the tools 100. The respective methods implemented by the tools can be performed during mapping calculations after the inverse solution, the output of which can be utilized to generate a corresponding graphical visualization (e.g., the graphical output 18 of FIG. 1).

By way of example, the tools 100 can include a phase computation method 102 that is programmed to compute corresponding phase data 104 (e.g., corresponding to the phase data 14 of FIG. 1). The phase computation 102 can be computed on the processed reconstructed electro grams (e.g., those provided by the post-inverse solution processing 24 of FIG. 1 or 80 of FIG. 4), in which signal content outside of the range of physiological frequencies of interest (e.g., about 4-10 hertz) have been removed from the reconstructed electrogram signals.

As one example, the phase computation 102 can be implemented using a Hilbert transform to obtain the corresponding phase data 104 for the respective signals across the entire cardiac envelope. Other types of signal decomposition methods can be utilized. The phase data 104 thus can represent one or more time intervals for which the reconstructed electrograms have been constructed.

As a further example, let $-\pi$ be an arbitrary beginning of the cycle; then $\pi$ is the beginning of the next cycle. Each point in time in between is assigned a phase value between $[-\pi, \pi]$ in an increasing manner. For instance, assume that the obtained phase is the phase of a complex number of magnitude 1; that way, each respective cycle can be converted into one circle with center 0 in the complex space.

By way of example, let x be a reconstructed cardiac electrogram in a given location on the cardiac envelope. In order to find a phase signal that meets the above requirements for a given x, the phase space 'theory' can be used:

any real temporal signal can be seen as the projection on the real axis of a complex signal.

Thus, given x, one can find a complex signal X such that $x(t)=\Re(X(t))$ for all t, where $\Re$ is the real part of X. We denote $\Phi_X$ the argument of this complex signal: $\Phi_X(t)=\arg(X(t))$ to represent the computed phase for a given reconstructed and filtered electrical signal on the cardiac envelope. Given X, $\Phi_X$ is unique; but given x, it exists an infinite number of signals X. The following are several possible solutions for X that match $x(t)=\Re X(t))$ or at least $\tilde{x}(t)=\Re(X(t))$, where $\tilde{x}$ corresponds to the interesting (e.g., relevant) part of x (denoted herein as $\tilde{x}$) for the diagnostic that is extracted from the signals via processing techniques disclosed herein.

$$X(t)=\tilde{x}(t)+i\tilde{x}(t-\tau), \quad \text{Eq. 2}$$

where $\tau$ has to be estimated $$X(t)=\tilde{x}(t)+i\hat{x}(t) \quad \text{Eq. 3}$$

where $\hat{x}(t)$ is the Hilbert transform of $\tilde{x}(t)$;
In such case, X can be called the analytic signal of $\tilde{x}(t)$ and thus can be represented as follows:

$$X(t)=\tilde{x}(t)+i\partial_t\tilde{x}t \quad \text{Eq. 4}$$

$$X(t)=\tilde{x}(t)+i\int\tilde{x}(t)dt \quad \text{Eq. 5}$$

Or any X such that $\tilde{x}(t)=\Re(X(t))$, such as corresponding to a complex wavelet of x, for instance.

In order to compute the phase data 104 and perform phase mapping, to produce a unique solution (translate one cycle into a value between $[-\pi, \pi]$), a requirement for X is to get one circle around (0,0) for each cycle. This is accomplished by the preprocessing disclosed herein (e.g., FIGS. 3-5) to remove noise, irrelevant oscillation of the signals to extract the salient features of the X, thereby increasing the accuracy and reproducibility of aforementioned technique of phase mapping. The phase information can be computed for several segments of data at various points in time to make the analysis robust in terms of temporal and spatial consistency. The phase information from multiple data segments in the same patients can be combined using various computational and visualization techniques as disclosed herein.

Figure 9:
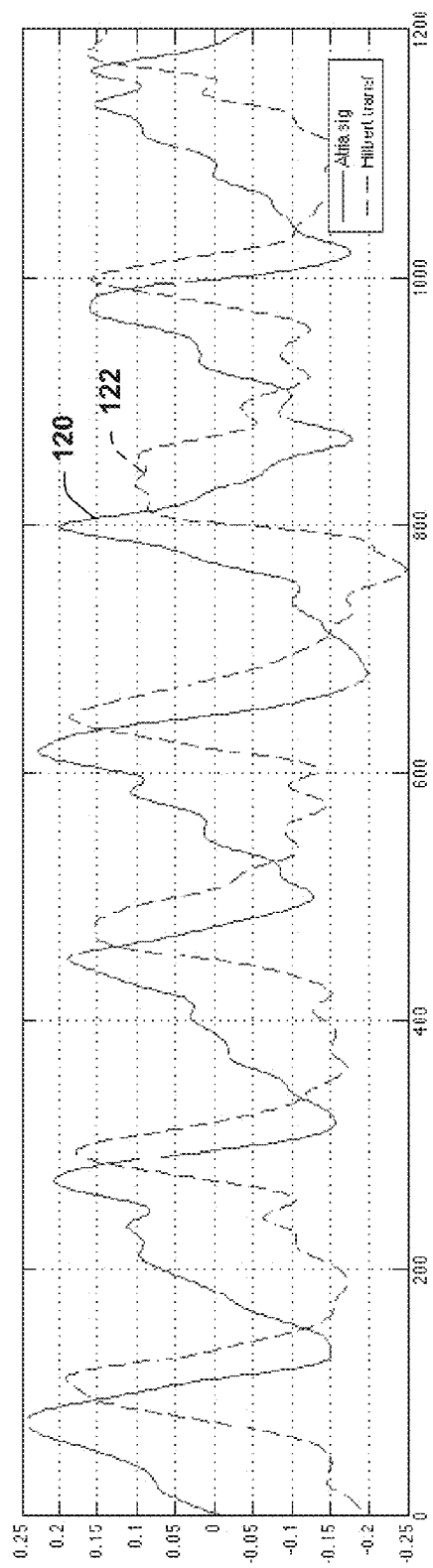
FIG. 9 depicts an example of an atrial signal and a corresponding transformation thereof.

FIG. 9 depicts an example of the processed atrial signal 120 as well as the Hilbert transformation of such signal demonstrated at 122, which corresponds to the computed phase data 104. Thus, the phase data can provide corresponding phase signals for each location (e.g., about 2000 or more points) on the cardiac envelope for one or more intervals for which the electrical data has been obtained.

Figure 10:
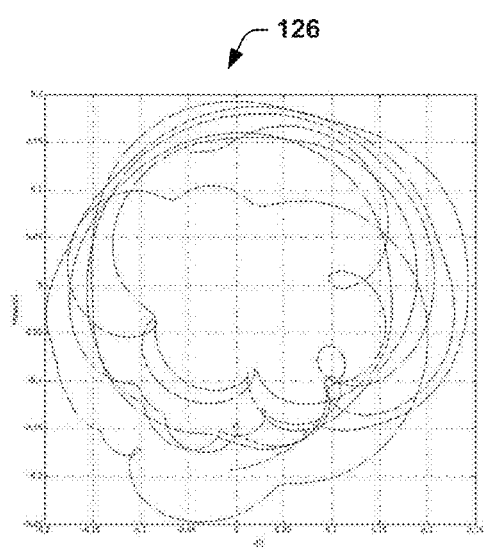
FIG. 10 depicts an example of phase for an atrial signal plotted in the complex plane.
Figure 11:
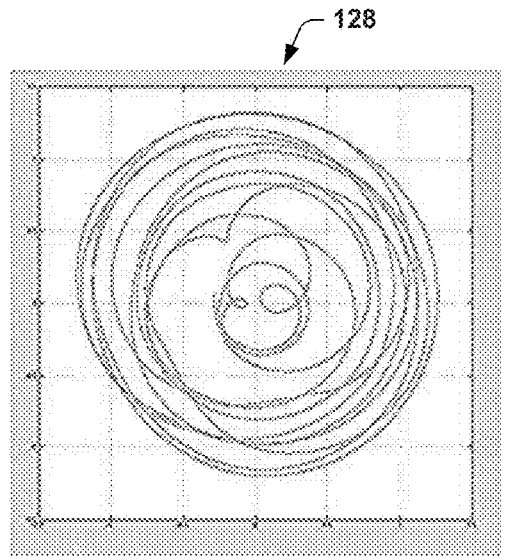
FIG. 11 depicts an example of for a ventricular signal plotted in the complex plane.

FIG. 10 depicts an example of an atrial signal plotted in a complex plane in which the real axis corresponds to the signal itself and an imaginary axis corresponds to the Hilbert transform of such signal. FIG. 11 is an example of a ventricular fibrillation signal plotted in the same way as FIG. 10.

For each phase signal computed at each respective location across the cardiac envelope from on the reconstructed electrograms, a corresponding phase map or other information can be generated and displayed for evaluation, such as to facilitate diagnosis and/or treatment of an arrhythmia, such as AF or VF. The corresponding phase signal can be displayed on a map for each electrogram location on a 3-D geometry corresponding to the cardiac envelope (e.g., such as the epicardial surface) of a patient's heart. Since a property of the phase is that $-\pi$ equals $\pi$, the color coding range or other scale utilized to visualize phase should be implemented to reflect this circular property of the phase signals. The phase map can be displayed as an integral phase at a given instant in time for each of the locations across the surface concurrently. Additionally, the map can be displayed as an animated phase map to demonstrate temporal patterns of the phase spatially across the surface. The 3-D surface can be rotated in response to a user input to show other portions of the surface according to the phase signals that have been computed as disclosed herein. Examples of different phase maps that can be generated are disclosed herein at FIGS. 14-23.

Referring back to FIG. 8, the phase calculator tools 100 can include a phase singularity computation 106 that is programmed to compute a location of a phase singularity. A phase singularity can be useful for diagnosis as a location in an atrial or ventricle at which all phases meet. On a phase map in which the computed phase is represented spatially by a color scale, a phase singularity corresponds to an area at which all colors in the corresponding color scale for the phase map occur at a common location. For instance, a phase singularity is demonstrated in a phase map 200 of FIG. 13 as the area designated "PS", which is the location on an anterior right atrium of a given patient's heart.

As mentioned above, a phase singularity occurs at a spatial location when all phases meet. This can be determined as an integral of phase gradient. By way of example, from a mathematical definition, at a given time t, a phase singularity occurs at the location x if $$\int_L \nabla\Phi(t)\cdot dr = \pm 2\pi, \quad \text{Eq. 6}$$

where $\phi(t)$ is the phase value computed on a close contour L around x.

Figure 24:
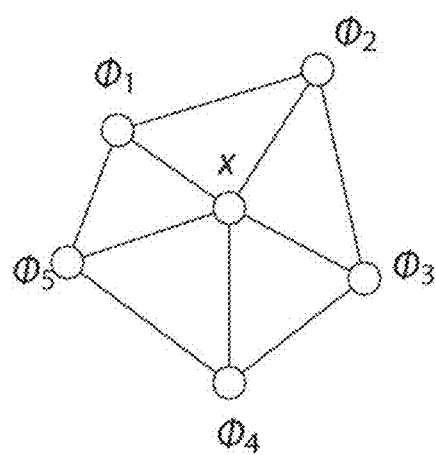
FIG. 24 depicts an example of a neighbor diagram of part of a cardiac envelope.

Each location and time satisfying Eq. 6 thus can be considered a singularity point (i.e., a rotor core). Here the heart surface (or other cardiac envelope) can be represented by a mesh structure, and the value of the integral of Eq. 6 can be estimated by a summation of changes in phase along the close contour around location X, such as follows:

$$\sum_{(X_i, X_j)\in N} (\Phi_{X_i}(t)-\Phi_{X_j}(t)) \quad \text{Eq. 7}$$

where N are the neighboring locations of x in the mesh surface sorted in a clockwise order relative to x, and $x_i$ and $x_j$ are adjacent locations, as demonstrated in the neighbor diagram depicted in FIG. 24.

In the example of FIG. 24, location x is surrounded by a set of neighbors each having respective phase values $\phi 1$, $\phi 2$, $\phi 3$, $\phi 4$, and $\phi 5$. The information of the rotor cores can be represented on a dynamic map to track their location and their trajectory in space over time. Alternatively, the information of the rotor cores can be averaged over time to get a single map for the entire episode.

The phase calculator tools 100 can include a focal source calculator 107 that is programmed to determine a location of one or more focal points based on phase data 104. The focal source calculator 107 thus can compute focal activation and identify a focal source of one or more wavefronts based on the phase signals represented by the data 104. A given location x can be defined as a focal source if the wavefront spreads from X to its neighbors (using the Neighbor Diagram of FIG. 24). At a given time t, the activation wavefronts are located where the phase equals $\pi/2$. It follows that X is a focal location if its phase value when the wavefront is passing the X location is earlier that the phase at the same instant of its neighbors. In the Neighbor Diagram of FIG. 24, a location X can be determined (by focal source calculator 107) as being a focal source if:

$$\exists t_1 \text{ such that } \Phi_X(t_1) \in [\pi/2-\epsilon, \pi/2+\epsilon] \text{ and } \Phi_X(t_1) > \Phi_i(t_1), i=1\ldots 5 \qquad \text{Eq. 8}$$

While there are 5 neighbors in this example of FIG. 24, there may be any number of neighbors in other examples. The foregoing identification of a focal source can be utilized to generate one or more corresponding visualizations, such as to graphically map an indication of the number of discharges for one or more foci. Each such map can be computed over one or more time intervals to provide spatially and temporally consistent data for the entire heart. In some examples, indications of focal activity (provided by calculator 107) and rotor activity (provided by computation 106 and/or 108) can be visualized in separate maps. In other examples, the focal activity and rotor activity can be aggregated and visualized concurrently in a single map to facilitate understanding fibrillation mechanisms.

In addition to identifying location of phase singularities in a 3-dimensional map, the tools 100 demonstrated in FIG. 8 can also include rotor identification 108 and rotor characterization 112. The rotor identification 108 can be programmed to compute statistics about location and trajectory of a given rotor spatially over time. Such statistics can include averaging the location of a rotor core over a time interval or over more than one time interval such as to generate a single map for a given rotor which may cover one or more episodes. For example, the rotor characterization functions 112 can be programmed to compute various statistics, such as can include statistics (e.g., mean, standard deviation and median) of activation wave fronts for each reconstructed electrogram location across the three dimensional cardiac envelope.

Additionally or alternatively, the rotor characterization function 112 can compute statistics (e.g., mean, standard deviation, median and the like) between two consecutive activations for each location across the cardiac envelope. As yet another example, the rotor characterization function 112 can be programmed to compute statistics (e.g., mean, standard deviation, median and the like) of rotor characterization for each location across the cardiac envelope.

The rotor characterization function 112 can include an interval selector that can select one or more time intervals in response to a user input. In addition to characterizing a given interval, other actions can be taken with respect to multiple intervals that have been selected (e.g., in response to a user input). For example, the rotor characterization can be programmed to combine intervals to display phase maps for the selected plurality of intervals. The rotor characterization function 112 further can, in response to a user input, compare computed statistics and data between different time intervals that have been selected by the user. For example, different intervals can have different lengths; however, the number of activation wave fronts per unit time can be computed for each and compared to ascertain additional information about wave fronts and numbers of rotor cores, for example. Such other information can include the number of rotor cores, the number of activations of focal sources as well as the location of focal sources across the cardiac envelope over time.

Figure 15:
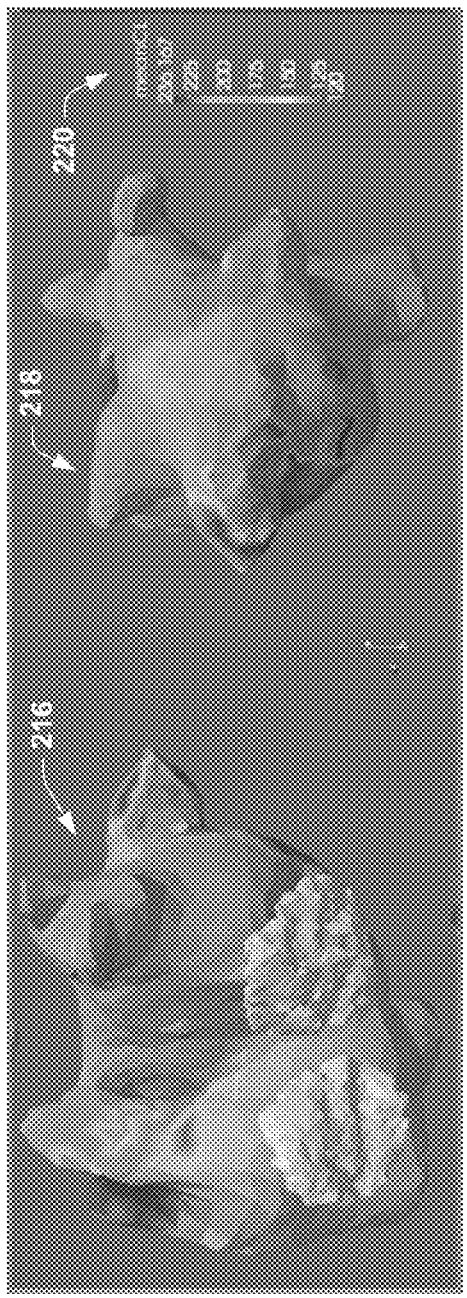
FIG. 15 depicts an example of a cycle length map.

The tools 100 can also include a cycle length computation function that is programmed to compute cycle length from the computed phase signals. Additionally, the cycle length computation can include computing statistics of cycle length that can vary during a user selected time interval during fibrillation or other arrhythmia. Based on the filtering that has been performed, including the pre-inverse solution processing and post-inverse solution processing, these signals reflect those that correspond to true atrial or ventricular depolarizations. For example, the cycle length computation can compute cycle length of an atrial fibrillation over a selected time interval. A corresponding map can be generated to demonstrate statistics of the computed cycle length, such as corresponding to a mean cycle length that is displayed on a three dimensional representation of the heart. An example of a cycle length map demonstrating mean cycle length by a color scale, which can be generated from the computed cycle length, is shown in FIG. 15.

Other information that can be computed by the tools 100, including the rotor characterization 112, can include the integral phase gradient (see, e.g., Eqs. 6 or 7) such as to demonstrate the spatial consistency of a rotor core on the 3-D representation of the heart. For example, the integral phase can be computed from a phase map by setting upper and lower thresholds above which corresponding integral phase can be determined for each location across the surface (e.g., including multiple chambers concurrently). A corresponding integral phase gradient map can be generated (see, e.g., FIG. 14) to demonstrate phase singularities.

Still another example of rotor characterizations 112 can include computing temporal frequency of rotor core position. Such temporal frequency can be computed for a single time interval for which the electrical activity data has been acquired. The rotor characterization function 112 can also combine multiple intervals and in turn compute the temporal frequency across the combined aggregate set of intervals. In addition to combining intervals, the rotor characterization function can be programmed to compare multiple intervals in separate maps to provide a visual comparison for a user.

Figure 12:
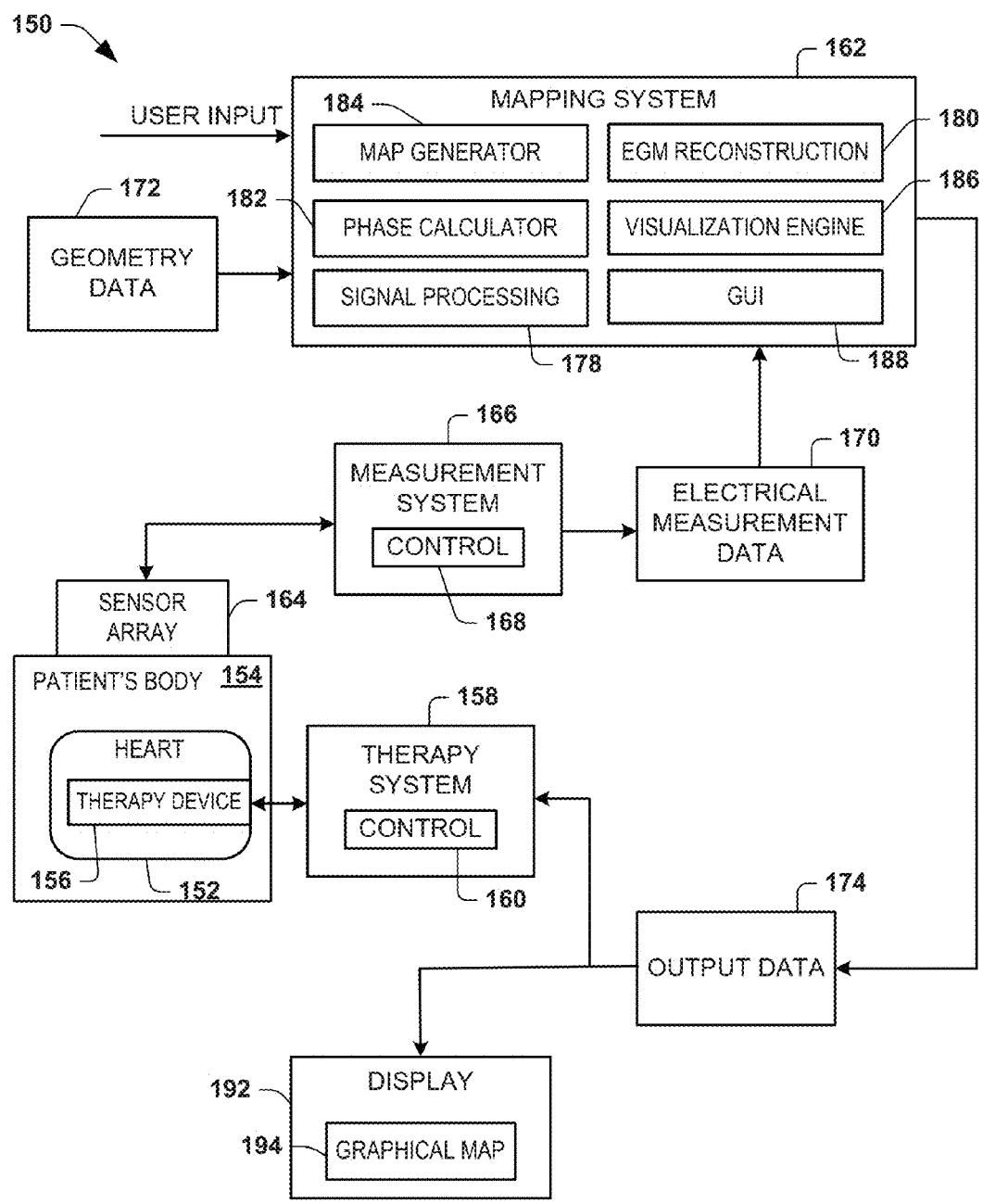
FIG. 12 depicts an example of a diagnostic and treatment system.

FIG. 12 depicts an example of a system 150 that can be utilized for performing diagnostics and/or treatment of a patient. In some examples, the system 150 can assess of the heart 152 in real time as part of a diagnostic or treatment procedure, such as to help a physician determine parameters for delivering a therapy to the patient (e.g., delivery location, amount and type of therapy). For example, a catheter, such as a pacing catheter or ablation catheter, having one or more therapy delivery devices 156 affixed thereto can be inserted into the body 154 as to contact the patient's heart 152, endocardially or epicardially. Those skilled in the art will understand and appreciate various type and configurations of therapy delivery devices 156 that can be utilized, which can vary depending on the type of treatment and the procedure.

In some examples, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other ablation mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

The therapy system 158 can be located external to the patient's body 154 and be configured to control therapy that is being delivered by the device 156. For instance, the therapy system 158 includes control circuitry 160 that can communicate (e.g., supply) electrical signals via a conductive link electrically connected between the device (e.g., electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic controls). One or more sensors (not shown) can also communicate sensor information back to the therapy system 158. The position of the device 156 relative to the heart 152 can be determined and tracked intraoperatively via an imaging modality (e.g., fluoroscopy, xray), a mapping system 162, direct vision or the like. The location of the device 156 and the therapy parameters thus can be combined to provide corresponding therapy parameter data.

Before, during and/or after providing a therapy via the therapy system 158, another system or subsystem can be utilized to acquire electrophysiology information for the patient. In the example of FIG. 12, a sensor array 164 includes one or more electrodes that can be utilized for recording patient activity. As one example, the sensor array 164 can correspond to a high-density arrangement of body surface sensors (e.g., greater than 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements of sensing electrodes can be used as the sensor array 164. The array can be a reduced set of electrodes, which that does not cover the patient's entire torso and is designed for measuring electrical activity for a particular purpose (e.g., an array of electrodes specially designed for analyzing AF and/or VF).

One or more sensors may also be located on the device 156 that is inserted into the patient's body. Such electrode can be utilized in conjunction with the sensor array 164 for mapping electrical activity for an endocardial surface such as the wall of a heart chamber. Additionally, such electrode can also be utilized to help localize the device 156 within the heart, which can be registered into an image or map that is generated by the system 150.

In each of such example approaches for acquiring patient electrical information, including invasively, non-invasively, or a combination of invasive and non-invasive sensors, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog or digital information.

The control 168 can also be configured to control the data acquisition process for measuring electrical activity and providing the measurement data 170. The measurement data 170 can be acquired concurrently with the delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective data 170 and therapy parameters to facilitate the evaluation and analysis thereof.

The mapping system 162 is programmed to combine the measurement data 170, corresponding to electrical activity of the heart 152, with geometry data 172 by applying appropriate processing and computations (e.g., as disclosed with respect to FIGS. 1-4) to provide corresponding output data 174. The output data 174 can be represent or characterize phase across the cardiac envelope (e.g., on a surface of the heart 152).

As one example, the output data 174 can correspond to phase maps or another characterization based on phase data computed for an epicardial surface of the patient's heart 152, such as based on electrical data that is acquired non-invasively via sensors 164 distributed on the surface of the patient's body 154. Alternatively or additionally, the output data 174 can include a potential map reconstructed for a surface of a patient's heart such as based on the same electrical activity that is recorded via body surface sensors 164 to generate phase data.

Since the measurement system 166 can in some examples measure electrical activity for the entire heart concurrently, the resulting output data (e.g., phase characterizations and/or other electrocardiographic maps) thus can also represent concurrent data for the heart in a temporally and spatially consistent manner. The time interval for which the output data/maps are computed can be selected based on user input. Additionally or alternatively, the selected intervals can be synchronized with the application of therapy by the therapy system 158.

The mapping system 162 includes signal processing methods, demonstrated at 178. The signal processing methods 178 can include the pre-inverse solution and post-inverse solution processing disclosed herein (e.g., preprocessing 50 of FIG. 2, preprocessing 70 of FIG. 3 and post-processing 80 of FIG. 4). Thus, the signal processing can preprocess the electrical measurement data 170 by extracting relevant signal content in response to a user input. For example, the user input can identify a type of fibrillation for which mapping is to be performed, such as AF or VF. In response to the selected type of phase evaluation, the signal processing can be configured accordingly to implement appropriate filtering and baseline removal for removing extraneous signal content and unwanted oscillations, as disclosed herein.

Electrogram reconstruction 180 can then compute an inverse solution on the processed signals to provide corresponding reconstructed electrograms based on the process signals and the geometry data 172. The reconstructed electrograms thus can correspond to electrocardiographic activity across a cardiac envelope and can be static (three-dimensional at a given instant in time) or be dynamic (e.g., four-dimensional map that varies over time).

As disclosed herein, the cardiac envelope can correspond to an actual three dimensional surface of a patient's heart, which surface can be epicardial or endocardial. Alternatively or additionally, the cardiac envelope can correspond to a surface that resides between the epicardial surface of a patient's heart and the surface of the patient's body where the sensor array 164 has been positioned. Additionally, the geometry data 172 that is utilized by the electrogram reconstruction 180 can correspond to actual patient geometry, a generic model or a combination thereof.

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. The resulting segmented image data can be converted into a two-dimensional or three-dimensional graphical representation that includes the region of interest for the patient.

Alternatively, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the geometry data 172 can be acquired using nearly any imaging modality (e.g., x-ray, ultrasound, computed tomography, magnetic resonance imaging, or the like) based on which a corresponding representation can be constructed, such as described herein. Such imaging may be performed concurrently with recording the electrical activity that is utilized to generate the patient electrical measurement data 170 or the imaging can be performed separately (e.g., before the measurement data has been acquired).

The reconstructed electrogram data computed by the EGM reconstructions method (e.g., inverse solution) 180 can further undergo signal processing 178 such as according to the post-processing methods disclosed herein (e.g., post-inverse solution processing 80 of FIG. 4). Following the post-inverse solution processing that is performed by signal processing function 178, a phase calculator 182 can compute phase data for each of the signals (e.g., for over 1000 points) as disclosed herein. The resulting phase can be stored as phase data in memory and utilized by a map generator 184 to generate corresponding high resolution output data 174.

A visualization engine 186 can provide the output data 174 corresponding to a graphical representation for of phase information. Parameters associated with the visualization, such as including selecting a time interval, a type of information that is to be presented in the visualization and the like can be selected in response to a user input via a corresponding visualization GUI 188. The mapping system 174 thus can generate corresponding output data 174 that can provided by the visualization engine as a corresponding graphical output in a display 192, such as including an electrocardiographic phase map 194.

In addition to the mapping system 162 generating phase maps and phase characterization maps for fibrillation intervals, other types of electrocardiographic mapping can be utilized such as including activation maps, dominant frequency maps and the like. For example, the display 192 can include one or more regions for displaying phase map data concurrently with corresponding activation or dominant frequency maps to facilitate diagnosis and evaluation of AF or VF.

FIGS. 13 through 23 depict examples of phase maps and related graphical representations that can be generated via the systems and methods system disclosed herein.

Figure 13:
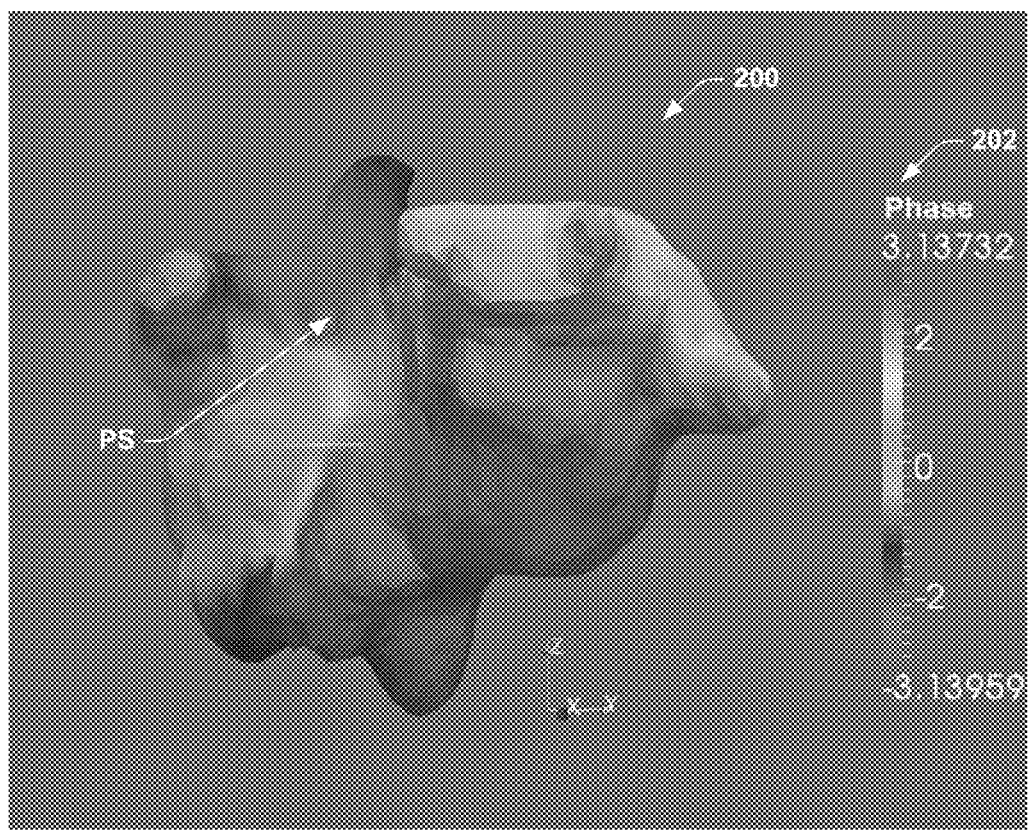
FIG. 13 depicts an example of a phase map.

FIG. 13 depicts an example of a phase map 200 that is rendered on a graphical representation of a heart. The map 200 includes a color scale 202 corresponding to the phase (e.g., between $\pm\pi$) computed for each of the locations across the three dimensional surface displayed in the map. In the example of FIG. 13, a rotor core is demonstrated at PS, which corresponds to a single location (e.g., a region, such as a two-dimensional spatial area) at which all phases meet. It is to be appreciated that, in other examples, more than one rotor may exist at a given time across the surface of the heart and that the approach disclosed herein can demonstrate each such phase singularity in a single 3D graphic representation since the phase data is computed based on electrical data that is obtained for the entire surface of the heart simultaneously for a given time interval.

Figure 14:
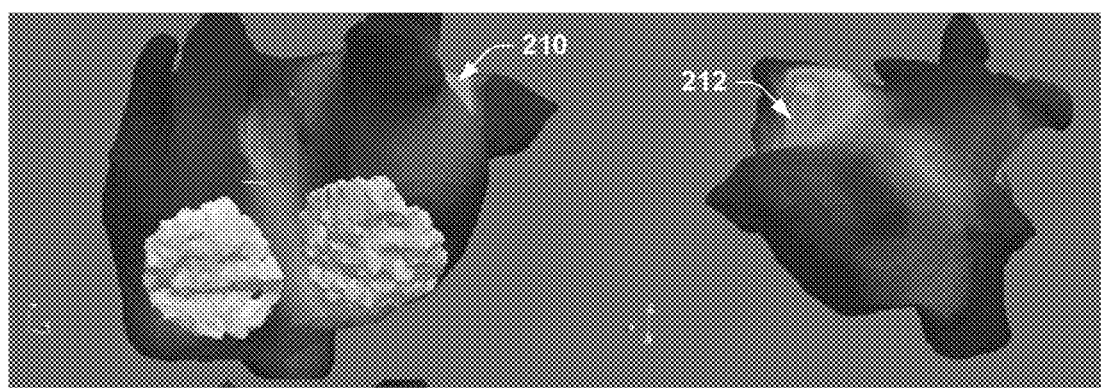
FIG. 14 depicts an example of a phase map demonstrating rotor core identification.

FIG. 14 depicts an example of a graphical map (e.g., an integral phase gradient map) of a heart demonstrating location of the rotor core for an AF case that is computed over a 500 millisecond time interval. In the example of FIG. 14 rotor cores are demonstrated at 210 and 212 in each of the 3D maps. The dark regions in the maps correspond to locations where no rotor core was determined to be anchored (e.g., according to Eqs. 6 or 7). The data utilized to generate the maps in FIG. 14 can be determined by a phase singularity or rotor identification function (e.g., executable code corresponding to 106 or 108 of FIG. 8).

FIG. 15 illustrates an example of a cycle length map that can be generated by a mapping system. In the example of FIG. 15, the cycle length has been computed as a mean cycle length for phases that occur over a 500 millisecond time interval, which can be selected by a user. The mean cycle length is plotted across the three dimensional geometry of the heart. The color coding scale 220 can be utilized to characterize statistics (e.g., median, standard deviation) computed for cycle length as well as the dominant frequency across a color spectrum, such as ranging from 120 milliseconds to about 230 milliseconds. In the example of FIG. 15 each of the maps 216 and 218 is demonstrated in different orientations for the same heart in three dimensional space such as to depict temporally consistent cycle length for different surface regions of the heart.

Figure 16:
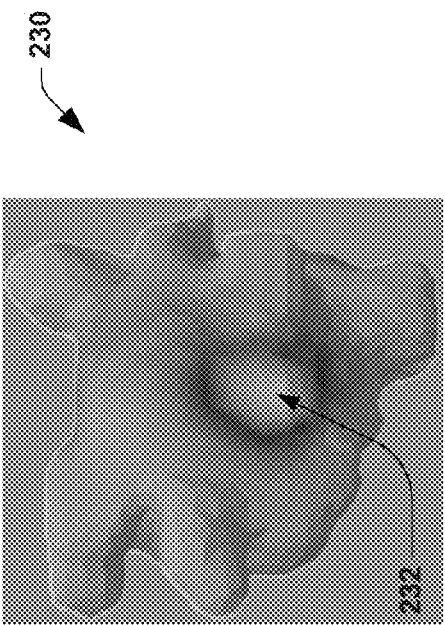
FIG. 16 depicts an example of an electrocardiographic map demonstrating a singularity.

FIG. 16 depicts an example of an electrocardiographic map 230 demonstrating a phase map corresponding to integral phase computed over a cardiac envelope (e.g., multiple chambers, such as can be the entire epicardial surface) for a time interval. In the example of FIG. 16 the information presented in the map can represent spatial consistency of a rotor core on cardiac envelope, indicated at area 232. The phase characteristics in the map 230 can represent a summation of integral phase across one or more intervals, such as by plotting data when the computed phase is greater than a predetermined phase threshold that has been established. The threshold can be user selected (e.g., via GUI 188 of FIG. 12) to change the sensitivity of the information being presented.

Figure 17:
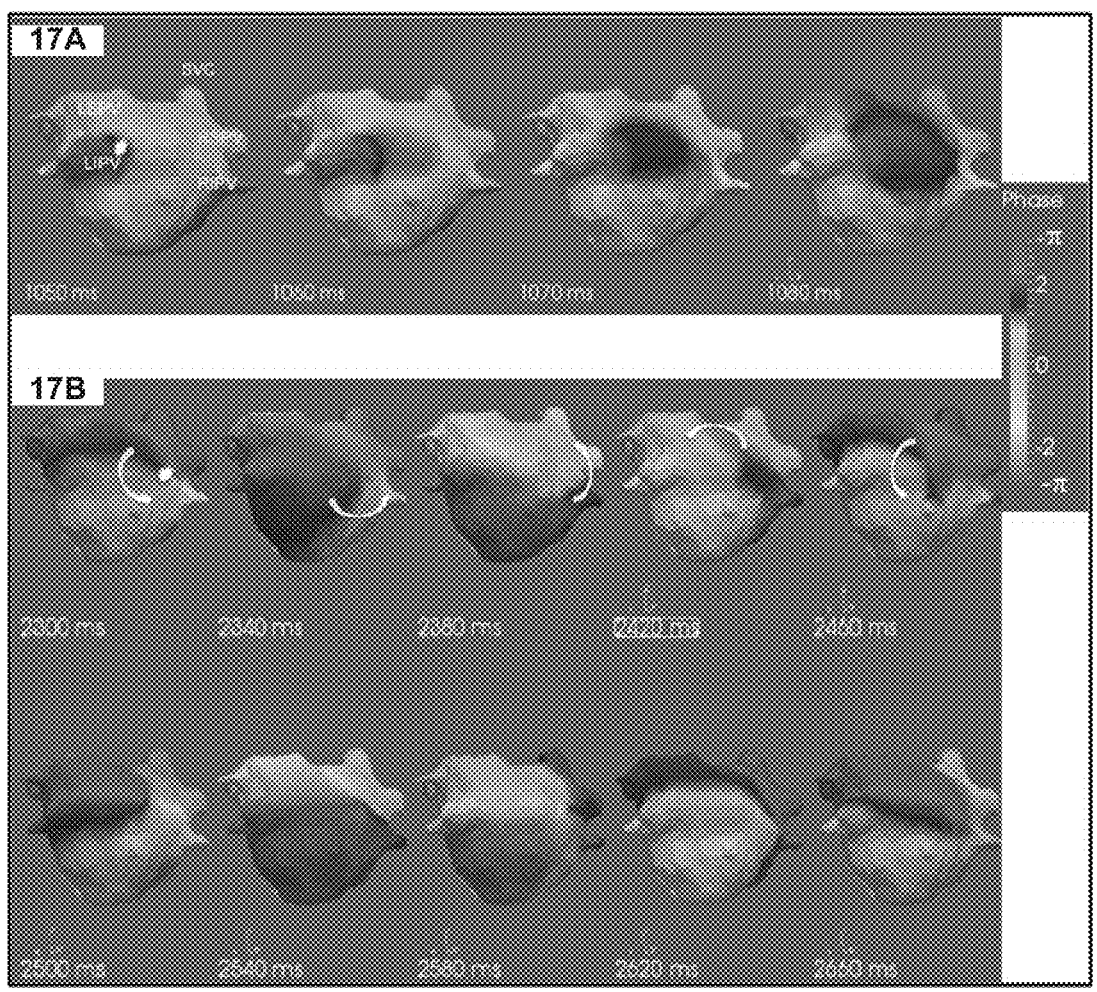
FIG. 17 depicts an example of an animated phase map for a heart that can be generated based on the systems and methods disclosed herein.

FIG. 17 depicts an example of a phase map demonstrating an animated or movie format at a plurality of different instances over a time interval. In FIG. 17, the upper portion designated 17A demonstrates phase maps from 1050 milliseconds to 1080 milliseconds. In the lower portion designated 17B, a time range from 2300 milliseconds 2660 milliseconds. An animated rendering of the phase map over time can help a user identify rotor movement and interactions between rotors.

In addition to plotting a computed phase in an animated manner or static manner similar to that shown in FIG. 17, other visualization mapping methods can be utilized such as to identify rotor trajectories and other rotor characteristics such as disclosed herein.

Figure 18:
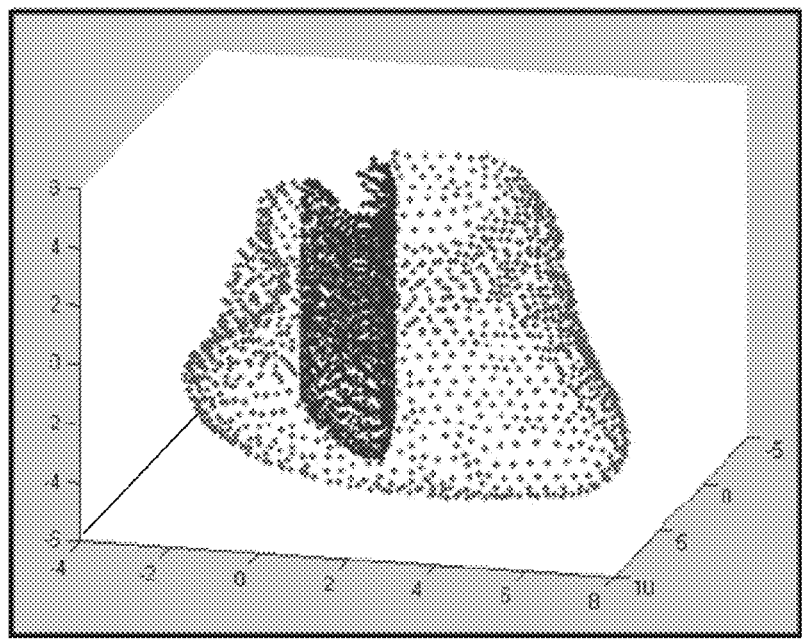
FIGS. 18 through 20 depict different parts of an algorithm that can be utilized to determine location and trajectory of rotor cores based on phase map data computed by systems and methods disclosed herein.
Figure 19:
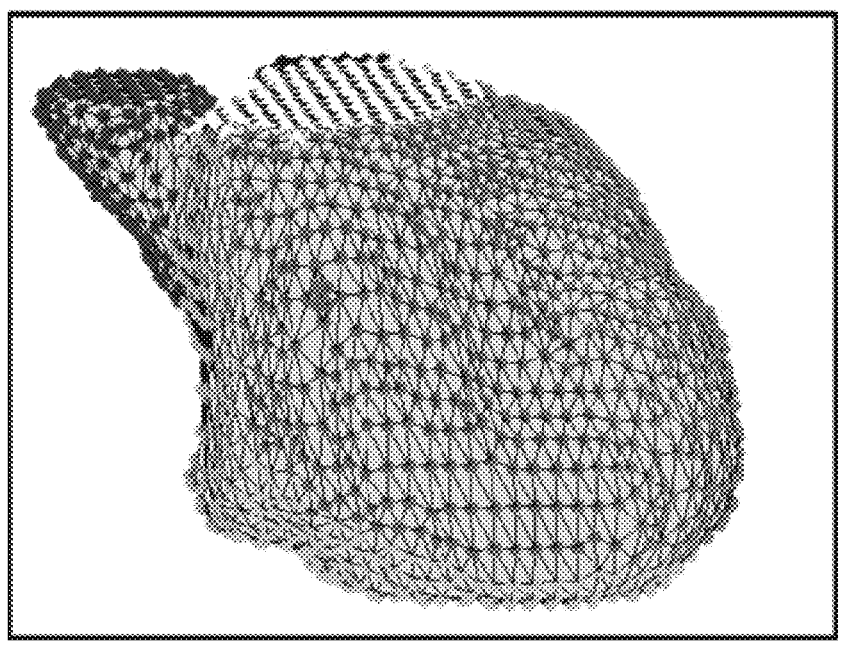

By way of example, using each point on the cardiac envelope (e.g., corresponding to heart epicardial surface), the corresponding surface can be projected onto a cylinder such as shown in the example of FIG. 18. The corresponding cardiac envelope or heart surface can be segmented into multiple regions of interest such as based upon the anatomical location in relevance to a given analysis. FIG. 19 demonstrates the points being segmented into multiple spatial regions by different color coding. Each segmented spatial region (e.g., from FIG. 19) can be mapped onto a two dimensional plane from the projected cylinder points of FIG. 18.

Figure 20:
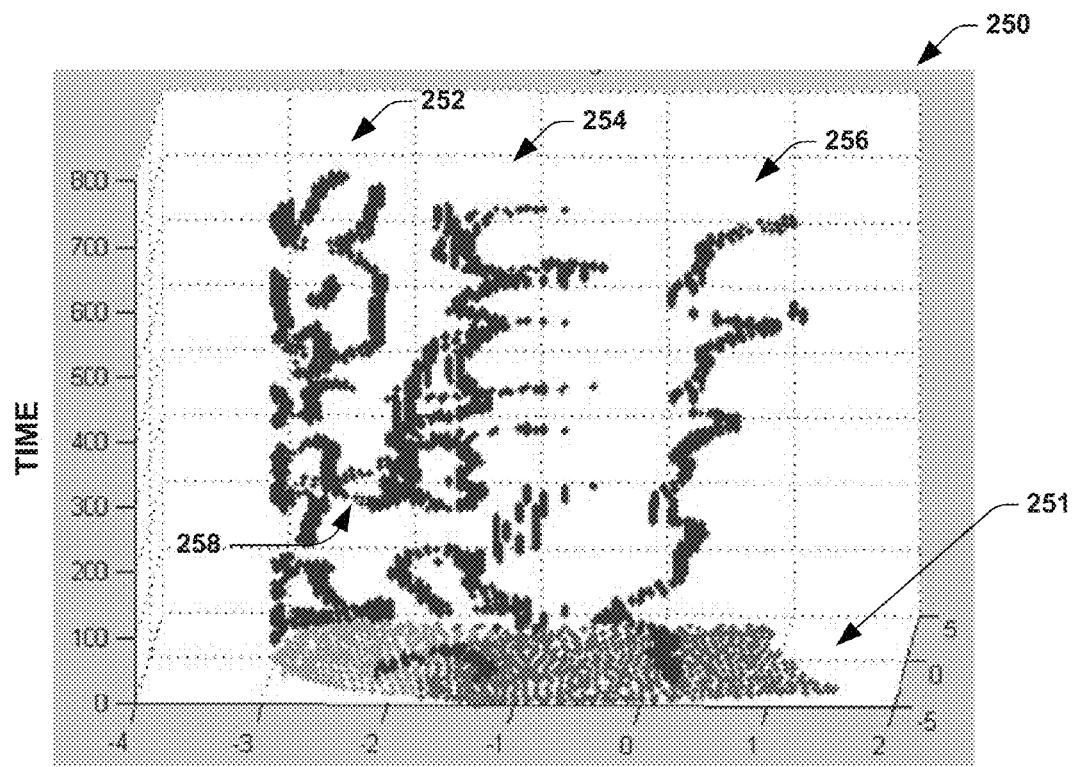

Stated differently, FIGS. 18-19 demonstrate intermediate steps of how to arrive at the plot depicted in FIG. 20. That is, FIGS. 18 and 19 demonstrate how each region of the geometry can be divided and projected onto a 2D surface for the rotor trajectory and characterization analysis. FIG. 18 shows the projection process of the geometry and FIG. 19 shows how each of the regions of the heart can be identified for the 2D surface. After the 2D projection, the regions can be displayed as a single region or as combinations of multiple regions.

FIG. 20 depicts a plot in which the segmented region or regions are projected onto a 2D plane 251, such as can be determined based on the analysis of the surface spatial regions demonstrated in FIGS. 18 and 19. Other forms of analysis, such as rotor trajectory tracking, can also be derived from such analysis. Also demonstrated in FIG. 20 is a vertical axis corresponding to time. From the plot 250, several rotor characteristics can be calculated for each identified rotor core 252, 254 and 256, such as including chirality and annular velocity. The characterization methods can identify a rotor core and the trajectory of the core can be determined over a time interval. For instance, since each of the cores are identified on a two dimensional surface projection, a given surface is spatially represented relative to its neighboring surfaces. Thus, the plot and corresponding rotor movement and rotor trajectory over time can be tracked across respective surface projections. Interactions between rotors and rotor fragmentations between respective rotors in the surface regions can also be identified. The surface projections 251 demonstrated in FIG. 20 are spatially related by overlapping the calculations, which can be used to identify rotor cores that migrate across corresponding surface projections.

In the example of FIG. 20, three rotor cores are demonstrated at 252, 254 and 256 over time. The rotor 256 remains spatially fairly stationary in the beginning (e.g., from time 0 to about 400 milliseconds) and then rotates around the spatial projection 251 later in the cycle time. The rotors 252 and 254 interact across the respective region, as indicated at 258, near 300 to 350 milliseconds.

Once rotor cores are identified spatially and interactions determined, the identified rotor core trajectories can be projected back onto a corresponding region of a 3-D surface to visualize the corresponding rotor movement in a map that varies over time (see, e.g., FIG. 17). After a rotor core has been identified spatially in a graphical map of cardiac anatomy, a catheter design can be generated for use in ablating the tissue where the rotor core occurs. The catheter design can include an identification of the number and spatial arrangement of electrodes. In some examples, the catheter design can identify one of a plurality of preconfigured catheters, such as by model number. In other examples, the catheter design can correspond to a custom configuration dimensioned and configured with an arrangement of electrodes specific for ablating the tissue region where one or more rotor cores have been identified.

In addition, a rotor interaction map can be produced to visualize rotor interactions in a graphical manner. For example, different color codings or other markings can be placed on the 3-D visualization of the heart to identify such interactions. Chiralty can be viewed on the rotor interaction map by showing a symbol within each circle or square that indicates the direction of rotor core spin. The annular velocity can also be displayed in a map as a color intensity of the lines which shows the rotor interactions on the map. Additionally, annular velocity may also be displayed as revolutions per second and fit to a corresponding color scale that can also be presented on the 3-D graphical map.

Figure 21:
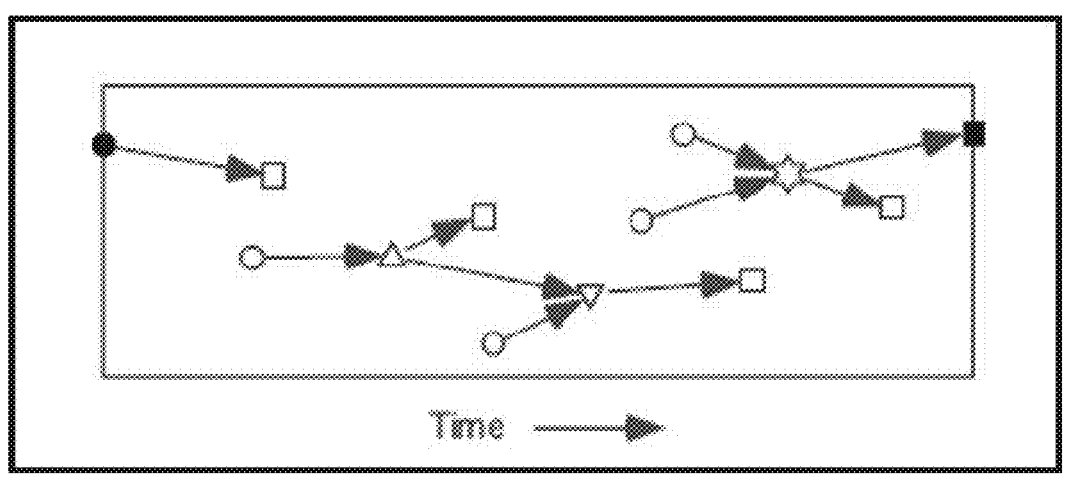
FIG. 21 depicts an example of a graph demonstrating rotor movement as a function of time that can include fragmentation and interaction between respective rotors.
Figure 22:
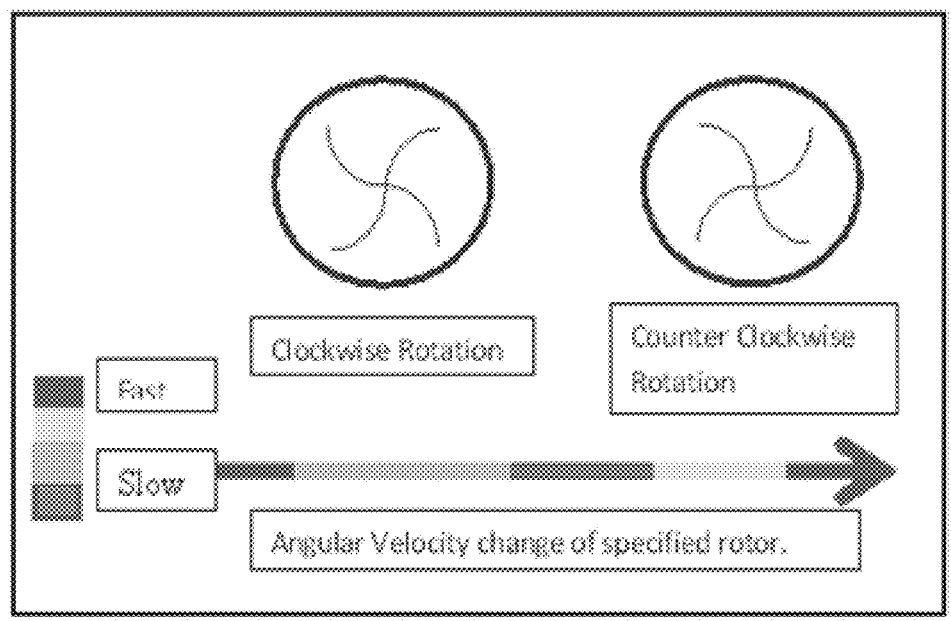
FIG. 22 depicts an example of graphical elements that can be applied to a phase map to demonstrate different rotor characteristics.

Additional maps can be produced such as shown on FIGS. 21 and 22. In FIG. 21, a rotor core interaction map is demonstrated such as can be generated based on the computations and interactions between rotor cores demonstrated in FIG. 20. FIG. 22 demonstrates another example of information that can be presented on a graphical map to show chirality (e.g., direction of rotation for a given rotor) and color change that can be applied to a map to indicate annular velocity of each respective rotor that has been identified.

Figure 23:
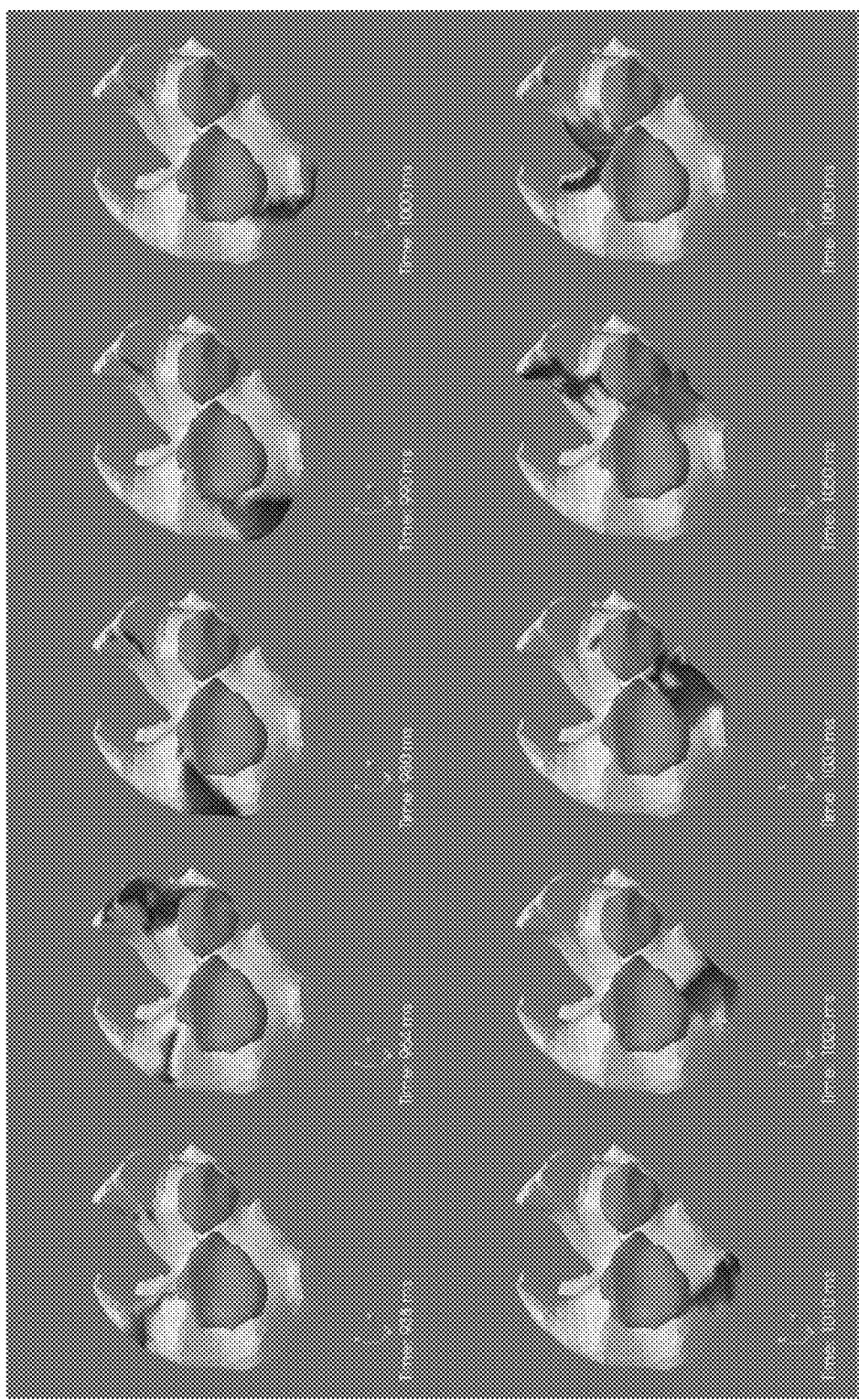
FIG. 23 depicts an animated representation of phase maps for atrial flutter.

In addition to AF and VF, the phase computation disclosed herein can also be utilized to provide a graphical representation for atrial flutter, such as shown in the example of FIG. 23. In FIG. 23, only phases within a small integral phase have been color coded such as can be used to facilitate tracking of the propagation pathway for atrial flutter such as corresponding to a counterclockwise rotation of phase relative to a heart valve. As an example, one or more maps or an animated map can be shown to demonstrate a situation where the computed phase $\phi(x)$=constant, such as shown in FIG. 23 for the case of atrial flutter. In a color version of this figure, for example, the condition $\phi(x)=\pi/2$ can be graphically represented in purple and all other conditions can be represented in gray (or other different color). Similar diagnostic information can be visualized for other types of arrhythmia, such as to visualize instances of constant phase for atrial fibrillation or ventricular fibrillation.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 25. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 25:
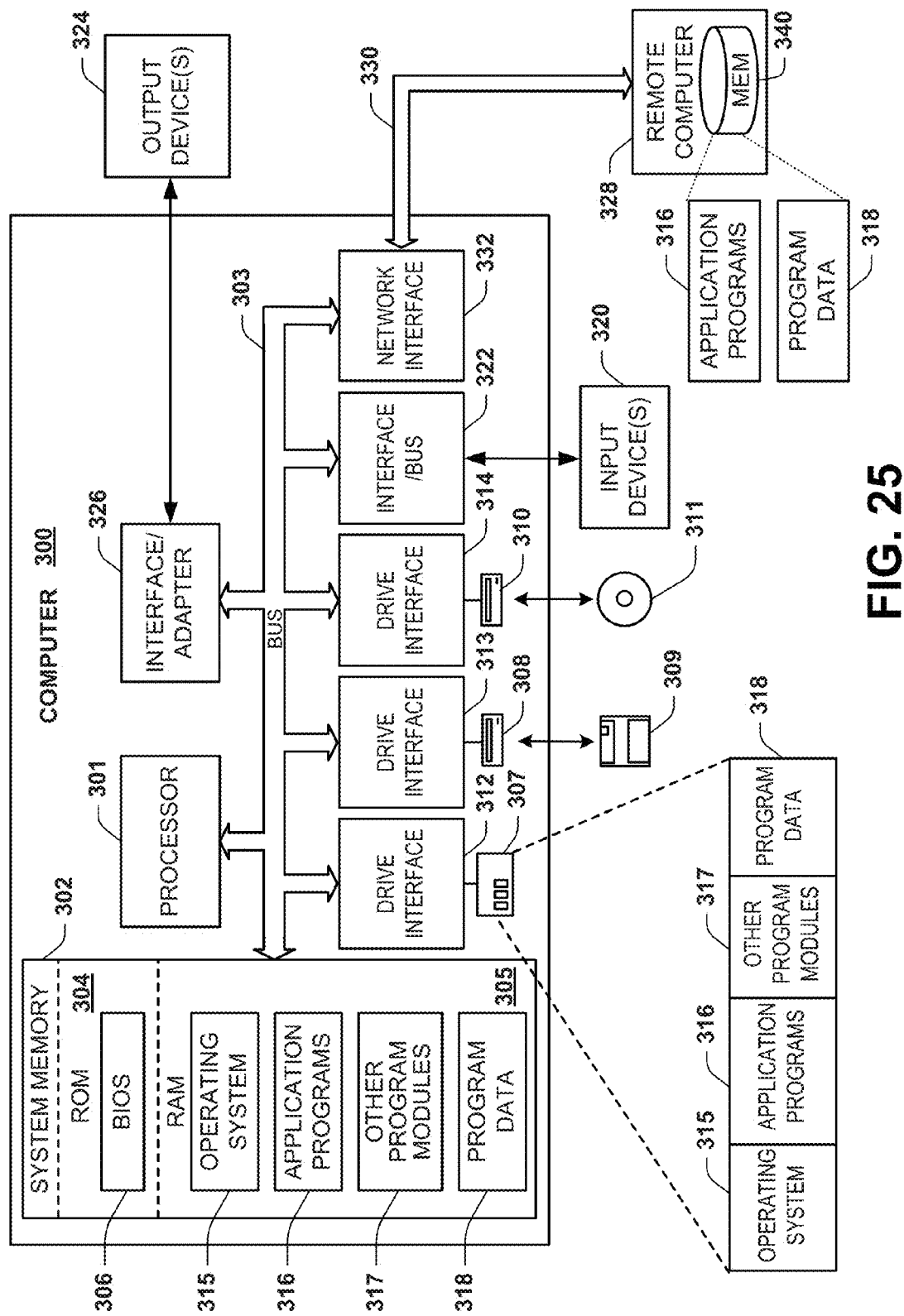
FIG. 25 depicts an example computing environment in which systems and methods can be implemented.

In this regard, FIG. 25 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/ nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to process signals and compute phase data as disclosed herein. The application programs and program data can also include functions and methods programmed to generate a phase map or other electrocardiographic map as disclosed herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A system comprising:
   a non-transitory memory to store machine readable instructions and data; and
   a processor to access the memory and execute the instructions for performing a method that comprises:

converting processed electrical data, corresponding to non-invasive electrical data obtained from a patient for at least one time interval, to corresponding reconstructed electrical signals on a predetermined cardiac envelope, the reconstructed electrical signals being spatially and temporally consistent;

computing phase data based on the reconstructed electrical signals.

2. The system of claim 1, wherein the method further comprises generating an output based on the computed phase data, wherein the output comprises a phase map for the cardiac envelope.

3. The system of claim 2, wherein the method further comprises determining a location of at least one phase singularity on the cardiac envelope and displaying the location of the at least one phase singularity in the phase map for the cardiac envelope.

4. The system of claim 2, wherein the method further comprises determining a location of at least one focal source on the cardiac envelope and displaying the location of the at least one focal source in the phase map for the cardiac envelope.

5. The system of claim 1, wherein the method further comprises:

computing rotor characteristics based on the phase data; and generating an output based on the computed phase data over the at least one time interval, wherein the output comprises a rotor map.

6. The system of claim 1, further comprising an arrangement of electrodes configured to cover a predetermined portion of a patient's torso and detect electrical activity non-invasively from an exterior surface of the patient's torso, the detected electrical activity corresponding to the non-invasive electrical data.

7. The system of claim 6, further comprising a therapy device configured to deliver therapy to cardiac tissue at a spatial location identified based on the computed phase data.

8. The system of claim 1, wherein the method further comprises computing temporal frequency of a spatial location for a rotor core over at least one time interval.

9. The system of claim 1, wherein the method further comprises:

estimating an indication of an integral of phase gradient for the cardiac envelope; and generating an output comprising an integral phase gradient map based on the estimated indication to present spatially and temporally consistent phase information for multiple chambers of the patient's heart corresponding to the cardiac envelope.

10. The system of claim 1, wherein prior to the converting, the method further comprises preprocessing non-invasive electrical data obtained from the patient for at least one time interval to extract signal features determined to contribute to arrhythmia and providing the processed electrical data corresponding to the extracted signal features, the reconstructed electrical signals being derived from the processed electrical data.

11. The system of claim 10, wherein the cardiac envelope is an epicardial surface and the arrhythmia is at least one of atrial fibrillation, atrial tachycardia, ventricular tachycardia and ventricular fibrillation.

12. The system of claim 1, wherein following the converting, the method further comprises the processing the reconstructed electrical signals to provide post-processed reconstructed electrical signals, the computed phase data being computed based on the post-processed reconstructed electrical signals.

13. The system of claim 1, wherein prior to the converting, the method further comprises preprocessing non-invasive electrical data obtained from a patient for at least one time interval to remove signal features determined not to contribute to a predefined arrhythmia and to provide the processed electrical data, the reconstructed electrical signals being derived from the processed electrical data.

14. The system of claim 13, wherein the preprocessing further comprises removing signal features from the non-invasive electrical data that are due to ventricular electrical activity to increase specificity for an atrial type of arrhythmia.

15. The system of claim 14, wherein the removing signal features further comprises at least one of implementing cancellation of QRS-waves or cancellation of T-waves from signals represented by the non-invasive electrical data.

16. The system of claim 13, wherein the method further comprises selectively controlling the preprocessing that is performed depending on which of an atrial or ventricular arrhythmia is selected as the predefined arrhythmia in response to a user input, wherein if the user input selects the atrial arrhythmia, the preprocessing being programmed to remove signal features representing ventricular electrical activity.

17. The system of claim 1, wherein the reconstructed electrical signals provide electrical information for over 1000 locations distributed across the cardiac envelope.

18. The system of claim 1, wherein the converting is performed by computing an inverse solution based on geometry that is at least one of actual geometry data acquired for a given patient and a generic anatomical model.

19. The system of claim 1, wherein the method is further programmed to compute an indication of cycle length based on the computed phase data.

20. The system of claim 1, wherein the reconstructed electrical signals are generated for each of a multitude of points residing on the predetermined cardiac envelope, and wherein the phase data is computed for the multitude of points based on the reconstructed electrogram signals based on geometry data.

* * * * *